United States Patent
Singh et al.

(12)

(10) Patent No.: US 9,835,632 B2
(45) Date of Patent: Dec. 5, 2017

(54) BIOMARKER PANEL FOR ASSESSMENT OF MUCOSAL HEALING

(71) Applicants: Nestec S.A., Vevey (CH); Katholieke Universiteit Leuven, Leuven (BE)

(72) Inventors: Sharat Singh, Rancho Santa Fe, CA (US); Severine Vermeire, Leuven (BE)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/213,243

(22) Filed: Jul. 18, 2016

(65) Prior Publication Data

US 2017/0010281 A1 Jan. 12, 2017

Related U.S. Application Data

(63) Continuation of application No. PCT/IB2015/050502, filed on Jan. 22, 2015.

(60) Provisional application No. 61/930,901, filed on Jan. 23, 2014.

(51) Int. Cl.
| | |
|---|---|
| *G01N 33/53* | (2006.01) |
| *G01N 33/68* | (2006.01) |
| *G01N 33/564* | (2006.01) |
| *G01N 33/74* | (2006.01) |
| *G06F 19/00* | (2011.01) |

(52) U.S. Cl.
CPC ....... *G01N 33/6893* (2013.01); *G01N 33/564* (2013.01); *G01N 33/6863* (2013.01); *G01N 33/74* (2013.01); *G06F 19/3431* (2013.01); *G01N 2333/4753* (2013.01); *G01N 2333/485* (2013.01); *G01N 2333/525* (2013.01); *G01N 2333/70503* (2013.01); *G01N 2333/70542* (2013.01); *G01N 2800/065* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 2008/0064113 | A1* | 3/2008 | Goix | C07K 16/2875 436/86 |
| 2014/0044667 | A1* | 2/2014 | Greff | A61K 8/042 424/78.05 |
| 2016/0052982 | A1* | 2/2016 | Cohen | A61K 47/48046 424/85.2 |

FOREIGN PATENT DOCUMENTS

WO 2012/154987 A1 11/2012

OTHER PUBLICATIONS

Paul, S. et al., "Therapeutic drug monitoring of infliximab and mucosal healing in inflammatory bowel disease: a prospective study," Inflammatory Bowel Diseases, 19:2568-76, 2013.
Van Moerkercke, W. et al., "405 High infliximab trough levels are associated with mucosal healing in Crohn's disease," Gastroenterology, 138(5):S-60, 2010.
Daperno, M. et al., "Results of the 2nd part scientific workshop of the ECCO (II): measures and markers of prediction to achieve, detect, and monitor intestinal healing in Inflammatory Bowel Disease," Journal of Crohn's and Colitis, 5(5):484-498, 2011.
Iskandar, H. et al., "Biomarkers in inflammatory bowel disease: current practices and recent advances," Translational Research, 159(4):313-325, 2012.
Tahara, Y., "Hepatocyte growth factor facilitates colonic mucosal repair in experimental ulcerative colitis in rats," J. Pharmacology and Experimental Therapeutics, 307(1):146-151, 2003.

\* cited by examiner

*Primary Examiner* — Jacob Cheu
(74) *Attorney, Agent, or Firm* — Kilpatrick Townsend and Stockton LLP

(57) ABSTRACT

The present invention provides methods for predicting the likelihood of mucosal healing in an individual with inflammatory bowel disease (IBD), including Crohn's disease and ulcerative colitis (UC). In addition, the present invention provides methods for monitoring the progression of mucosal healing in an individual with a disease such as IBD. Information on mucosal healing status derived from the use of the present invention can also aid in optimizing therapy and/or monitoring the therapeutic efficiency of an anti-TNFα inhibitor drug.

23 Claims, 8 Drawing Sheets

BIOMARKER PANEL FOR ASSESSMENT OF MUCOSAL HEALING

The present application is a continuation of PCT/IB2015/050502 filed Jan. 22, 2015, which claims priority to U.S. Provisional Patent Application No. 61/930,901, filed Jan. 23, 2014, the contents of which are hereby incorporated by reference in their entirety for all purposes.

BACKGROUND OF THE INVENTION

The assessment of mucosal healing plays a central role in the treatment course of inflammatory bowel diseases (IBD). Currently, ileocolonoscopy for the colon and terminal ileum and computerized tomography or magnetic resonance for the small bowel, are the standard methods for the evaluation of disease activity.

Achievement of mucosal healing has become an important new treatment goal for IBD patients as recently also supported by regulatory agencies. This more ambitious therapeutic goal was achieved after the introduction of the biological therapies against tumor necrosis factor alpha (TNF-α). Before, only corticosteroids, azathioprine and methotrexate were available to treat Crohn's disease (CD) and the healing rates observed with these agents are poor (Mary et al., *Gut*, 1989, 30:983-989; Colombel et al., *N. Engl., J. Med.*, 2010, 362:1383-1395; Peyrin-Biroulet et al., *Gut*, 2014, 63:88-95; Geagan et al., *N. Engl. J. Med.*, 2000; 342:1627-1632).

Several endoscopic activity scoring systems have been developed for CD and ulcerative colitis (UC), but some are complicated, especially for CD. Moreover, frequent endoscopic assessments are expensive and both the procedure as well as the preparation are uncomfortable to the patient. Therefore a high need exists for non-invasive, but accurate surrogate markers for assessment and prediction of mucosal healing. Previous efforts have identified several genetic, blood and fecal markers, but the sensitivity and specificity of the tests are often not sufficient for clinical practice (Daperno et al., J. Crohns Colitis, 2011, 5:484-498).

There is an unmet need in the art for non-invasive methods for predicting the likelihood of mucosal healing patients with inflammatory bowel disease. The present invention satisfies this need and provides related advantages as well.

BRIEF SUMMARY OF THE INVENTION

The present invention provides methods for the assessment of mucosal healing of a patient with inflammatory bowel disease including Crohn's disease and ulcerative colitis. In particular, the present invention comprises measuring a plurality of biomarkers to determine a cumulative biomarker score for determining the mucosal healing status, or as a surrogate for an endoscopic disease measurement scale.

As such, in one embodiment, the present invention provides a method for predicting the likelihood or the extent of mucosal healing in a subject. The methods for assessing mucosal healing in a subject include measuring the concentration or level of a set or a panel of biomarkers.

In one embodiment, the biomarkers include HGF, BTC, TWEAK and VCAM-1. The method comprises:
  (a) measuring the concentration or level of a plurality of biomarkers in a sample obtained from the subject, wherein the plurality of biomarkers comprises hepatocyte growth factor (HGF), betacellulin (BTC), tumor necrosis factor-related weak inducer of apoptosis (TWEAK) and vascular cell adhesion molecule 1 (VCAM-1);
  (b) comparing the concentration or level of each of the plurality of biomarkers to a cut-off value for each biomarker to assign an index value to the concentration or level of each biomarker;
  (c) determining a cumulative biomarker score by applying an algorithm to the index values; and
  (d) predicting an increased likelihood or the extent of mucosal healing in the subject based on the cumulative biomarker score.

In another embodiment, the biomarkers include HGF, BTC, the anti-TNFα trough level and VCAM-1. The method comprises:
  (a) measuring the concentration or level of a plurality of biomarkers in a sample obtained from the subject, wherein the plurality of biomarkers comprises hepatocyte growth factor (HGF), betacellulin (BTC), anti-TNFα trough level (e.g., IFX trough level) and vascular cell adhesion molecule 1 (VCAM-1);
  (b) comparing the concentration or level of each of the plurality of biomarkers to a cut-off value for each biomarker to assign an index value to the concentration or level of each biomarker;
  (c) determining a cumulative biomarker score by applying an algorithm to the index values; and
  (d) predicting an increased likelihood or extent of mucosal healing in the subject based on the cumulative biomarker score.

In some embodiments, the cumulative biomarker score is a surrogate for an endoscopic disease measurement scale.

In some embodiments, the subject has inflammatory bowel disease. In some instances, the inflammatory bowel disease is Crohn's disease or ulcerative colitis. In certain instances, the individual has Crohn's Disease.

In some embodiments, measuring in step (a) comprises performing a proximity dual detection assay, an immunoassay or a homogeneous mobility shift assay. In some instances, the proximity dual detection assay is Collaborative Enzyme Enhanced Reactive Immunoassay (CEER™).

In some embodiments, the index value is from 0 to 4; or 1 to 4 and based on whether the concentration or level of the biomarker is above or below the cut-off value such that the value of 4 is positively associated with mucosal healing.

In some embodiments, the cut-off value for HGF is less than about 11.42 CU/ml. In some instances, the cut-off value for HGF is from about 1 CU/ml to about 11.42 CU/ml.

In some embodiments, the cut-off value for BTC is greater than about 11.44 CU/ml. In some instances, the cut-off value for BTC is from about 11.44 CU/ml to about 100 CU/ml or more.

In other embodiments, the cut-off value for BTC is greater than about 10.3 CU/ml. In some instances, the cut-off value for BTC is from about 10.3 CU/ml to about 100 CU/ml or more.

In some embodiments, the cut-off value for TWEAK is greater than about 20.62 CU/ml. In some instances, the cut-off value for TWEAK is from about 20.62 CU/ml to about 100 CU/ml or more.

In some embodiments, the cut-off value for the anti-TNFα trough level (e.g., IFX trough level) is greater than about 5.8 μg/ml. In some instances, the cut-off value for the anti-TNFα trough level (e.g., IFX trough level) is greater than about 5.8 μg/ml to about 10 μg/ml.

In some embodiments, the cut-off value for VCAM-1 is less than about 420 µg/ml. In some instances, the cut-off value for VCAM-1 is from 1 µg/ml to about 420 µg/ml.

In some embodiments, comparing in step (b) comprises applying an algorithm incorporating the concentration or level of each of the plurality of biomarkers.

In some embodiments, the index value is from 1 to 4 based on a quartile score, such that quartile 1 is given an index value of 4, quartile 2 is given an index value of 3, quartile 3 is given an index value of 2 and quartile 4 is given an index value of 1.

In other embodiments, the index value is from 1 to 4 based on a quartile score, such that quartile 1 is given an index value of 1, quartile 2 is given an index value of 2, quartile 3 is given an index value of 3 and quartile 4 is given an index value of 4. In some instances, quartile 1 is given an index value of 1 for biomarkers, such as IFX trough and BTC.

In some embodiments, the quartile scores for BTC and TWEAK are inverted in the algorithm. In some instances, the algorithm in step (c) comprises summing the index values to determine the cumulative biomarker score.

In some embodiments, for example, when TWEAK is used, the cumulative biomarker score of 4 predicts an increased likelihood of mucosal healing in the subject. In other embodiments, for example, when the anti-TNFα drug trough level is used, a cumulative biomarker score of 16 indicates an increased likelihood of mucosal healing in the subject.

In some embodiments, the subject is receiving or being administered a TNFα inhibitor. In some instances, the TNFα inhibitor comprises one or more of REMICADE™ (infliximab), ENBREL™ (etanercept), HUMIRA™ (adalimumab), or CINZIA™ (certolizumab pegol). In some instances, the TNFα inhibitor comprises REMICADE™ (infliximab).

In some embodiments, the sample is selected from the group consisting of serum, plasma, whole blood, stool, peripheral blood mononuclear cells (PBMC), polymorphonuclear (PMN) cells, fine needle aspirate, and a tissue biopsy.

In some embodiments, the method further comprises performing the steps (a) to (d) at a second time point; comparing the prediction of mucosal healing at the first time point to that of the second time point; and determining whether the subject has maintained, decreased or increased mucosal healing at the second time point.

In another embodiment, the present invention provides a method for determining an endoscopic measurement score in a subject, the method comprising:
(a) measuring the concentration or level of each of a plurality of biomarkers in a sample obtained from the subject, wherein the plurality of biomarkers comprises at least two of the following biomarkers, which include hepatocyte growth factor (HGF), betacellulin (BTC), tumor necrosis factor-related weak inducer of apoptosis (TWEAK) and vascular cell adhesion molecule 1 (VCAM-1);
(b) comparing the concentration or level of the plurality of biomarkers to a cut-off value for each biomarker to assign an index value to the concentration or level of each biomarker;
(c) determining a cumulative biomarker score by applying an algorithm to the index values; and
(d) determining the endoscopic measurement score in the subject based on the cumulative biomarker score.

In certain instances, the user correlates the cumulative biomarker score to the endoscopic measurement score using a lookup table. In certain instances, at least three, or at least 4 biomarkers are used.

In some embodiments, the endoscopic measurement score is of the Crohn's Disease Endoscopic Index of Severity (CDEIS) system or the Simple Endoscopic Score in Crohn's Disease (SES-CD) system. The cumulative biomarker score of 4-6 can correspond to the CDEIS score of about less than 6 or the SES-CD score of about 0-4. In some instances, the cumulative biomarker score of 4-6 indicates that there is an at least 50% decrease in CDEIS score or SES-CD score compared to baseline or an earlier time point. In other instances, the cumulative biomarker score of 4-6 indicates the presence of mucosal healing. Optionally, the cumulative biomarker score of 14-16 indicates the absence of mucosal healing.

In yet another embodiment, the present invention provides a method for determining an endoscopic measurement score in a subject, the method comprising:
(a) measuring the concentration or level of each of a plurality of biomarkers in a sample obtained from the subject, wherein the plurality of biomarkers comprises at least two of the following biomarkers, which include hepatocyte growth factor (HGF), betacellulin (BTC), an anti TNFα drug trough level and vascular cell adhesion molecule 1 (VCAM-1);
(b) comparing the concentration or level of the plurality of biomarkers to a cut-off value for each biomarker to assign an index value to the concentration or level of each biomarker;
(c) determining a cumulative biomarker score by applying an algorithm to the index values; and
(d) determining the endoscopic measurement score in the subject based on the cumulative biomarker score.

In certain instances, the user correlates the cumulative biomarker score to the endoscopic measurement score using a lookup table. In certain instances, at least three, or at least 4 biomarkers are used.

In some embodiments, the endoscopic measurement score is of the Crohn's Disease Endoscopic Index of Severity (CDEIS) system or the Simple Endoscopic Score in Crohn's Disease (SES-CD) system. The cumulative biomarker score of 14-16 can correspond to the CDEIS score of about less than 6 or the SES-CD score of about 0-4. In some instances, the cumulative biomarker score of 14-16 indicates that there is an at least 500/o decrease in CDEIS score or SES-CD score compared to baseline or an earlier time point. In other instances, the cumulative biomarker score of 14-16 indicates the presence of mucosal healing. Optionally, the cumulative biomarker score of 4-6 indicates the absence of mucosal healing.

Other objects, features, and advantages of the present invention will be apparent to one of skill in the art from the following detailed description and figures.

BRIEF DESCRIPTION OF THE DRAWINGS

FIG. 4A illustrates the quartile analysis of the 181 serum sample for the four biomarkers (e.g., HGF, BTC, TWEAK or VCAM-1). Quartile score of 1 was assigned an index score of 4; quartile score of 2 was assigned an index score of 3; quartile score of 3 was assigned an index score of 2 and quartile score of 4 was assigned an index score of 1. FIG. 4B illustrates the association of the percentage of mucosal healing to the level of the biomarkers individually and to the sum of scores, for each quartile score. The sum of scores (e.g., cumulative index value) was calculated for the combination of the 4 markers. The scores for BTC and TWEAK were inverted in the calculation of the sum. Linear-by-linear association test was performed.

FIG. 7A illustrates a division of the marker levels into quartiles for HGF, BTC, IFX trough levels and VCAM-1. Levels in Q1-Q4 were given a score 4-1 for VCAM-1 and HGF, whereas levels in Q1-Q4 were given a score 1-4 for IFX trough and BTC. FIG. 7B is a representation of the number of samples in each quartile in the sum of quartiles. FIG. 7C shows the percentage of samples with observed mucosal healing associated with the quartile levels. The quartile of the sum of quartile scores was calculated for all 4 markers and a positive test result for all 4 markers was observed in 67% of the samples matched to mucosal healing.

DETAILED DESCRIPTION OF THE INVENTION

I. Introduction

Figure 1:
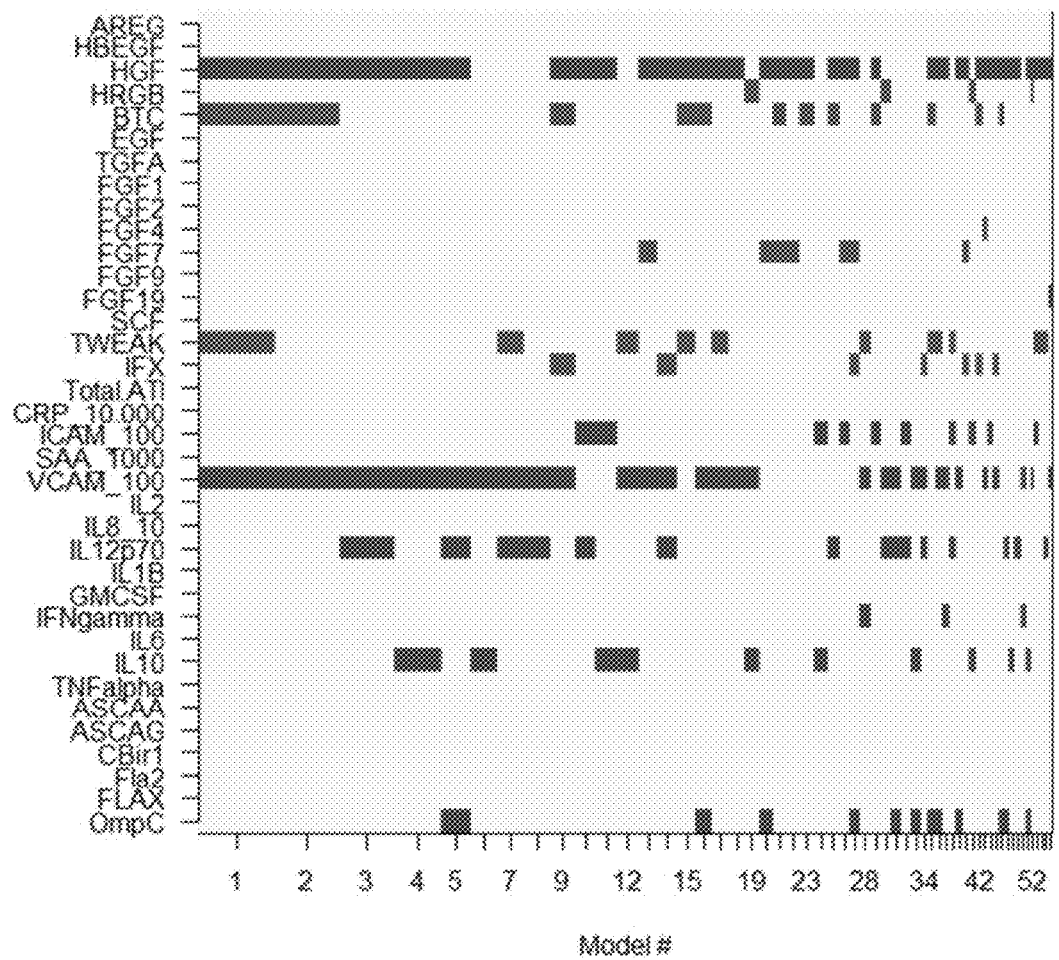
FIG. 1 illustrates the output plot in R for the multiple logistic regression analysis using the Bayesian model averaging method. Model selection based on the Bayesian information criterion (BIC) resulted in 56 models. In one embodiment, HGF, BTC, TWEAK and VCAM-1 were retained as the best predictors of mucosal healing in the final model.

Anti-TNFα drugs such as infliximab (IFX) and adalimumab (ADA), promote mucosal healing in inflammatory bowel disease (IBD) patients. In fact, in clinical trials, endoscopic evidence of mucosal healing (endoscopic disease measurement) is a marker of the anti-inflammatory action of biological anti-TNFα drugs.

One underlying principle of the present invention is that IBD such as Crohn's disease and ulcerative colitis is better understood when viewed as a wound of the intestinal mucosal. Like other wounds of epithelial tissue, three phases of healing occur. A subject having IBD and being treated with an anti-TNFα drug will progress through an inflammatory phase, a proliferation phase, and finally a remodeling phase. This mucosal healing mechanism occurs over time and is facilitated by anti-TNFα drugs while being treated.

Intestinal wound healing is thus a precise balance of migration, proliferation, and differentiation of the intestinal epithelial cells (IEC) adjacent to the wounded area. First, IECs surrounding the wound lose their columnar polarity, take on a flattened morphology, and rapidly migrate into the denuded area to restore barrier integrity in a process termed "epithelial restitution." Second, there is a proliferation of the mucosal epithelium to increase the pool of enterocytes available to resurface the defect. Last, maturation and differentiation of epithelial cells is needed to maintain barrier function. It is thus clear that mucosal healing in IBD in a tightly controlled process associated with suppression of inflammation and improvement of intestinal barrier function that is dependent on the balance of migration, proliferation and functional differentiation of IECs.

The inflammatory phase occurs first and during this phase, bacteria and foreign debris are removed from the wound. Inflammatory markers are present at their highest concentration levels during this phase. Next, the proliferative phase is characterized by tissue formation, epithelialization, and wound contraction. In this phase, epithelial cells that are activated by growth factors and repair factors proliferate and provide cover for the new tissue. During the remodeling phase, the wound contracts and is made smaller by the action of myofibroblasts, which establish a grip on the wound edges and contract themselves, thereby healing the wound. A person just beginning therapy will most likely be in the inflammation phase and progress with a proper therapeutic regimen to the remodeling phase. And eventually, the intestinal mucosa will be restored.

Using the invention provided herein, it is possible to predict the likelihood and extent of mucosal healing (e.g., progression through the phases of mucosal healing towards complete improvement thereof and endpoint) through the phases in a patient with inflammatory bowel disease including Crohn's Disease and ulcerative colitis. In addition, the present invention can be used to monitor a subject's progression through mucosal healing over a plurality of time points e.g., longitudinally over the course of the disease. The present invention can also be used to determine whether a patient has complete improvement of mucosal healing and without relapse. The invention also provides methods for confirmation of mucosal healing. Furthermore, the present invention provides methods for optimizing therapeutic efficiency for an anti-TNFα antibody therapy and for selecting an appropriate therapeutic regimen based on the mucosal healing status of the subject. In other embodiments, the present invention provides a biomarker panel as a surrogate for an endoscopic disease measurement, such as a CDEIS score or SES-CD score. The cumulative biomarker index can be used to predict a subject's CDEIS score or SES-CD score without the need of endoscopy.

II. Definitions

As used herein, the following terms have the meanings ascribed to them unless specified otherwise.

The term "mucosal healing" refers to the restoration of normal mucosal appearance of a previously inflamed region, and complete absence of ulceration and inflammation at the endoscopic and microscopic levels. Mucosal healing includes repair, remodeling and restoration of the mucosa, submucosa, and muscularis layers. It can also include neuronal and lymphangiogenic elements of the intestinal wall.

The term "progression of mucosal healing" refers mucosal healing over a period of time towards complete improvement (e.g., complete repair) of the intestinal mucosa. In some instances, the progression of mucosal healing toward complete improvement occurs over the course of months or the course of years. In certain instances, the anti-TNFα drug therapeutically heals the mucosa.

The terms "marker" and "biomarker" include any biochemical markers, serology markers, protein markers, genetic markers, and/or other clinical or echographic characteristics, that can be measured in a sample.

The term "marker score" or "biomarker score" includes an empirically derived score that is based upon an analysis of a plurality of markers such as, biochemical markers, serology markers, protein markers, genetic markers, and/or other clinical or echographic characteristics, level of anti-TNFα antibody, and level of anti-drug antibody. In one aspect, the concentration of the markers or their measured concentration values are transformed into an index value by a statistical algorithm. A biomarker score can be determined multiple times over the course of different time points over the course of the disease. In certain aspects, the biomarker score comprises or corresponds to a synthetic or human derived output, value, or cut-off value(s) which expresses the biological data in numerical terms.

The terms "TNF inhibitor", "TNF-α inhibitor," "TNFα inhibitor" and anti TNFα drug" are intended to encompass agents including proteins, antibodies, antibody fragments, fusion proteins (e.g., Ig fusion proteins or Fc fusion proteins), multivalent binding proteins, small molecule TNF-α antagonists and similar naturally- or nonnaturally-occurring molecules, and/or recombinant and/or engineered forms thereof, that, directly or indirectly, inhibits TNF a activity. The term "TNFα inhibitor" preferably includes agents which interfere with TNF-α activity. Examples of TNF-α inhibitors (anti-TNFα drug) include etanercept (ENBREL™, Amgen), infliximab (REMICADE™, Johnson and Johnson), human anti-TNF monoclonal antibody adalimumab (D2E7/HUMIRA™, Abbott Laboratories), CDP 571 (Celltech), and CDP 870 (Celltech), as well as other compounds which inhibit TNF-α activity, such that when administered to a subject suffering from or at risk of suffering from a disorder in which TNF-α activity is detrimental (e.g., IBD), the disorder is treated.

The term "subject," "patient," or "individual" typically refers to humans, but also to other animals including, e.g., other primates, rodents, canines, felines, equines, ovines, porcines, and the like.

The term "sample" as used herein includes any biological specimen obtained from a patient. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), and cellular extracts thereof. In some embodiments, the sample is whole blood or a fractional component thereof such as plasma, serum, or a cell pellet. In other embodiments, the sample is obtained by isolating PBMCs and/or PMN cells using any technique known in the art. In other embodiments, the sample is a tissue biopsy, e.g., tissue obtained from a site of inflammation such as a portion of the gastrointestinal tract or synovial tissue.

The term "Crohn's Disease Endoscopic Index of Severity" or "CDEIS" refers to an endoscopic measurement system that evaluates the following variables, deep ulceration (if present, score of 12; if absent, score of 0), superficial ulceration (if present, score of 6; if absent, score of 0), surface involved by the disease (measured in cm), and ulcerated surface (measured in cm) in the terminal ileum, ascending colon, transverse colon, descending and sigmoid colon and the rectum (See. e.g., Khanna et al., *Inflamm Bowel Dis*, 2014, 20(10):1850-1861 and the Table below).

TABLE

| | Rectum | Sigmoid & Left Colon | Transverse Colon | Right Colon | Ileum | TOTAL |
|---|---|---|---|---|---|---|
| Deep ulceration if present, score 12 if absent, score 0 | | | | | | |
| Superficial ulceration if present, score 6 if absent, score 0 | | | | | | |
| Surface involved by the disease (measured in cm*) | | | | | | |
| Ulcerated surface measured in cm*) | | | | | | |
| TOTAL | | | | | | a |
| Number (n) of segments totally or partially explored (1-5) | | | | | | n |
| Total A divided by n | | | | | | b |
| Ulcerated Stenosis if present anywhere, score 3 if absent, score 0 | | | | | | c |
| Non-Ulcerated Stenosis if present anywhere, score 3 if absent, score 0 | | | | | | d |
| TOTAL b + c + d | | | | | | |

From Khanna et al., Inflamm Bowel Dis, 2014, 20(10): 1850-1861

For partially explored segments and for the ileum, the 10 cm linear scale represents the surface effectively explored.

The term "Simple Endoscopic Score in Crohn's Disease" or "SES-CD" refers to an endoscopic measurement scale the grades the following variables: ulcer size (diameter 0.1-0.5 cm, 0.5-2 cm, or >2 cm), proportion of ulcerated surface (<10%, 10%-30%, or >30%), proportion of the surface area affected by any disease lesion (<500%, 50%-75%, or >75%), and stenosis (single, multiple, whether the colonoscopy passes through the narrowing), in the ileum, right colon, transverse colon, left colon, or rectum. Each variable is scored from 0-3, and a total score is calculated as a sum of all the variables in each intestinal segment.

| | SES CD score | | | |
|---|---|---|---|---|
| Variable | 0 | 1 | 2 | 3 |
| Presence of ulcers | None | Aphtous ulcers (Ø 0.1-0.5 cm) | Large ulcers (Ø 0.5-2 cm) | Very large ulcers (Ø >2 cm) |
| Ulcerated surface | None | <10% | 10-30% | >30% |
| Affected surface | Unaffected segment | <50% | 50-75% | >75% |
| Presence of narrowings | None | Single, can be passed | Multiple, can be passed | Cannot be passed |

| | Ileum | Right colon | Transverse colon | Left colon | Rectum | SUM |
|---|---|---|---|---|---|---|
| Presence of ulcers | | | | | | + |
| Ulcerated surface | | | | | | + |
| Affected surface | | | | | | + |
| Presence of narrowings | | | | | | = |
| | | Sum of all variables | | | | TOTAL |

From Khanna et al., Inflamm Bowel Dis, 2014, 20(10): 1850-1861

III. Detailed Descriptions of Embodiments

The methods described herein can be used for predicting the likelihood and extent of mucosal healing in a subject. In some embodiments, the subject has an inflammatory bowel disease. In some instances, the inflammatory bowel disease is Crohn's disease (CD) or ulcerative colitis (UC). In certain instances, the subject is being administered an anti-TNFα drug.

In some embodiments, the present invention provides a method for predicting the likelihood or extent of mucosal healing. The methods for assessing mucosal healing in a subject include measuring the concentration or level of a set or panel of biomarkers. In some embodiments, the cumulative biomarker score is a surrogate for an endoscopic disease measurement scale.

In one embodiment, the biomarkers include HGF, BTC, TWEAK and VCAM-1. The method comprises:

(a) measuring the concentration or level of a plurality of biomarkers in a sample obtained from the subject, wherein the plurality of biomarkers comprises hepatocyte growth factor (HGF), betacellulin (BTC), tumor necrosis factor-related weak inducer of apoptosis (TWEAK) and vascular cell adhesion molecule 1 (VCAM-1);

(b) comparing the concentration or level of each of the plurality of biomarkers to a cut-off value for each biomarker to assign an index value to the concentration or level of each biomarker;

(c) determining a cumulative biomarker score by applying an algorithm to the index values; and (d) predicting an increased likelihood or the extent of mucosal healing in the subject based on the cumulative biomarker score.

In another embodiment, the biomarkers include HGF, BTC, anti-TNFα drug trough level (e.g., IFX) and VCAM-1. The method comprises:

(a) measuring the concentration or level of a plurality of biomarkers in a sample obtained from the subject, wherein the plurality of biomarkers comprises hepatocyte growth factor (HGF), betacellulin (BTC), anti-TNFα drug trough level (e.g., IFX trough level) and vascular cell adhesion molecule 1 (VCAM-1);

(b) comparing the concentration or level of each of the plurality of biomarkers to a cut-off value for each biomarker to assign an index value to the concentration or level of each biomarker;

(c) determining a cumulative biomarker score by applying an algorithm to the index values; and (d) predicting an increased likelihood or extent of mucosal healing in the subject based on the cumulative biomarker score.

In some embodiments, the subject has inflammatory bowel disease. In some instances, the inflammatory bowel disease is Crohn's disease (CD) or ulcerative colitis (UC). In certain instances, the individual has Crohn's Disease.

In some embodiments, the subject has inflammatory bowel disease including Crohn's disease or ulcerative colitis. In certain instances, the subject will be administered an anti-TNFα drug, is being administered an anti-TNFα drug, or has been administered an anti-TNFα drug.

In some embodiments, the cut-off value is determined from a control subject with mucosal healing, a healthy control, or an IBD patient sample.

In some embodiments, measuring in step (a) comprises performing a proximity dual detection assay, an immunoassay or a homogeneous mobility shift assay. In some instances, the proximity dual detection assay is Collaborative Enzyme Enhanced Reactive Immunoassay (CEER™).

In some embodiments, for example when TWEAK is used, the index value is from 0 to 4 or 1 to 4 (e.g., 1, 2, 3 or 4) and based on whether the concentration or level of the biomarker is above or below the cut-off value. For example, for a given sample, a cumulative biomarker score can be 4 and is associated with mucosal healing.

In another embodiment, when the anti-TNFα drug trough level is used, a cumulative biomarker score can be 16 and is associated with mucosal healing.

In some embodiments, the cut-off value for HGF is less than about 11.42 CU/m, the cut-off value for BTC is greater than about 11.44 CU/ml, or the cut-off value for BTC is greater than about 10.3 CU/ml, the cut-off value for TWEAK is greater than about 20.62 CU/ml, the cute off value for IFX trough level is greater than 5.8 µg/ml and the cut-off value for VCAM-1 is less than about 420 µg/ml.

In some instances, the cut-off value for HGF is from about 1 CU/ml to about 11.42 CU/ml; the cut-off value for BTC is from about 10.3 CU/ml or 11.44 CU/ml to about 100 CU/ml or more; the cut-off value for TWEAK is from about 20.62 CU/ml to about 100 CU/ml or more; the IFX trough level is greater than about 5.8 µg/ml to about 10 µg/ml; and the cut-off value for VCAM-1 is from 1 µg/ml to about 420 µg/ml.

In some embodiments, comparing in step (b) comprises applying an algorithm incorporating the concentration or level of the plurality of biomarkers.

In some embodiments, the index value is from 1 to 4 based on a quartile score, such that quartile 1 is given an index value of 4, quartile 2 is given an index value of 3, quartile 3 is given an index value of 2 and quartile 4 is given an index value of 1.

In one embodiment, an index value is assigned based on the amount or level of the biomarker.

In one embodiment, an index value of 4 is indicative of mucosal healing, whereas an index value of 1 is associated with no mucosal healing.

In one embodiment, an index value of 1 is indicative of mucosal healing, whereas an index value of 4 is associated with no mucosal healing.

In some embodiments, the quartile scores for BTC and TWEAK are inverted in the algorithm. In some instances, the algorithm in step (c) comprises summing or adding the index values to determine the cumulative biomarker score.

Figure 4A:
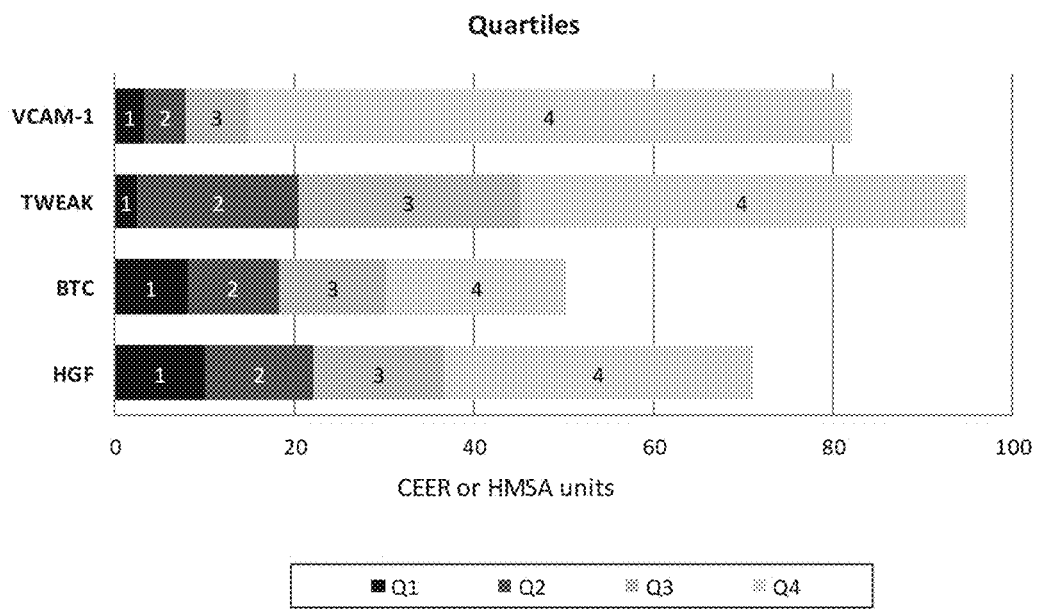
FIG. 4A-B illustrate quartile analysis and linear-by-linear association analysis of the levels of the markers and mucosal healing.
Figure 4B:
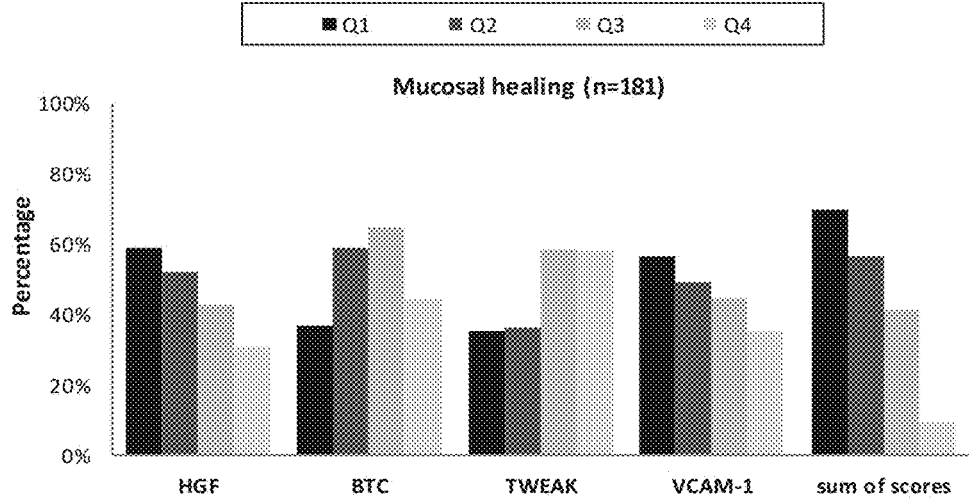

In some embodiments, the cumulative biomarker score of 4 predicts an increased likelihood of mucosal healing in the subject. The cumulative biomarker score can be 4, 5, 6, 7, 8, 9, 10, 11, 12, 13, 14, 15 or 16. In certain instances, when TWEAK is being used in the cumulative algorithm score, as shown in FIG. 4B, the cumulative biomarker score of 4-6 indicates mucosal healing, a cumulative biomarker score of 7-10 means partial mucosal healing, a cumulative score of 11-13 means some mucosal healing and a score of 14-16 means no mucosal healing.

Figures 7A, 7B, 7C:
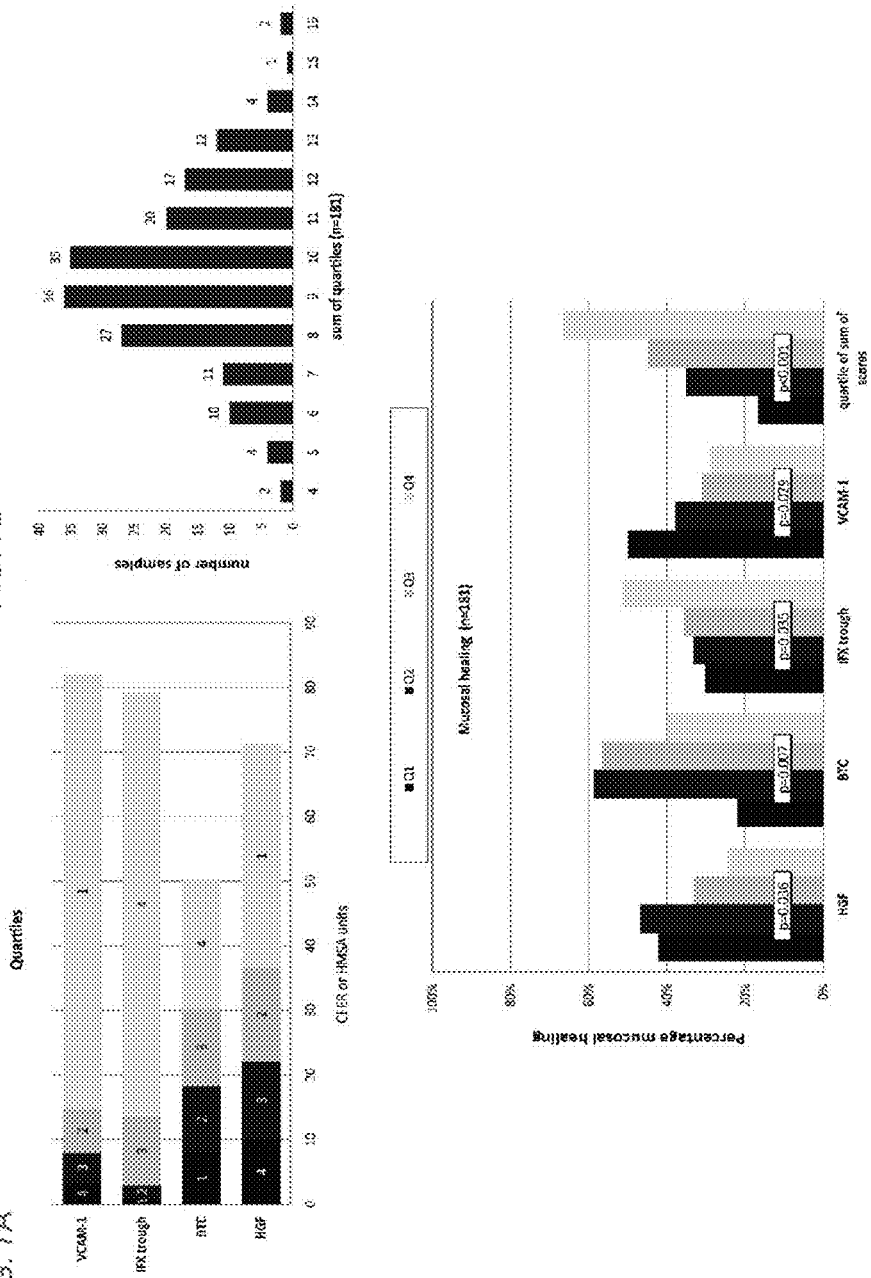
FIG. 7A-C illustrate a quartile analysis.

In some other embodiments, when the anti-TNFα drug trough level is used, as is shown in FIG. 7C, the cumulative biomarker score of 14-16 indicates mucosal healing, a cumulative biomarker score of 11-13 means partial mucosal healing, a cumulative score of 7-10 means some mucosal healing and a score of 4-6 means no mucosal healing.

In some embodiments, the subject is receiving a TNFα inhibitor. In some instances, the TNFα inhibitor comprises one or more of REMICADE™ (infliximab), ENBREL™ (etanercept), HUMIRA™ (adalimumab), and CINZIA™ (certolizumab pegol).

In some embodiments, the sample is selected from the group consisting of serum, plasma, whole blood, urine, stool, peripheral blood mononuclear cells (PBMC), polymorphonuclear (PMN) cells, fine needle aspirate, and a tissue biopsy. In other embodiments, the sample is a serum, plasma, whole blood or urine. In a preferred embodiment, the sample is serum.

In some embodiments, the method further comprises performing the steps (a) to (d) at a second time point; comparing the prediction of mucosal healing at the first time point to that of the second time point; and determining whether the subject has maintained, decreased or increased mucosal healing at the second time point.

In some embodiments, the plurality of time points comprises at least 1, 2, 3, 4, 5, 6, 7, 8, 9, 10, 11, 12, 13, 14, 15, 16, 17, 18, 19, 20, 25, 30, 35, 40, 45, 50, or more time points.

In some embodiments, an algorithm is used to predict relapse of a disease, or mucosal healing progression or an end point.

The methods described herein can be used to evaluate mucosal healing in an IBD individual receiving anti-TNFα therapy. In certain aspects, mucosal healing can change the natural course of the disease and/or reduce the development of long-term disease complications, such as bowel damage in CD and/or colorectal cancer in UC.

A. Biomarkers

Various biomarkers are suitable for the present invention. In certain instances, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or at least 36 markers are used. In some instances, 4 or more biomarkers are used. As shown below, various serum markers are shown and their various roles in mucosal healing are indicated.

Summary of serum markers

| Functional group | Specific function | Marker name | Abbreviation | NCBI Accession No. | GenBank Accession No. |
|---|---|---|---|---|---|
| Growth and repair factors | member of the epidermal growth factor family | Amphiregulin; colorectum cell-derived growth factor | AREG; AR; CRDGF | NP_001648 | AAA51781 |
| | member of the epidermal growth factor family | heparin-binding EGF-like growth factor; proheparin-binding EGF-like growth factor | HBEGF | NP_001936 | AAA35956 |
| | cellular growth, motility and morphogenic factor - mucosal repair and fibrosis | hepatocyte growth factor; hepatopoietin-A, scatter factor; | HGF; SF | NP_000592; NP_00101093; NP_00101092; NP_001010933; NP_001010934 | AAA52650 |
| | member of the epidermal growth factor family | heregulin beta EGF domain | HRGB | NP_001153477; NP_039250-NP_039253 | ABY70644 |
| | member of the epidermal growth factor family - mucosal repair | betacellulin; probetacellulin | BTC | NP_001720 | AAB25452 |

Summary of serum markers

| Functional group | Specific function | Marker name | Abbreviation | NCBI Accession No. | GenBank Accession No. |
|---|---|---|---|---|---|
| | cell growth, proliferation, and differentiation | epidermal growth factor; proepidermal growth factor; urogastrone | EGF | NP_001171601; NP_001171602; NP_001954 | AAH93731 |
| | cell proliferation, differentiation and development | transforming growth factor alpha; protransforming growth factor alpha | TGFA; TGFα | NP_001093161; NP_003227 | AAA61159 |
| | modifier of endothelial cell migration and proliferation, angiogenic factor, fibrosis | fibroblast growth factor 1; endothelial cell growth factor; heparin-binding growth factor | FGF1; aFGF; ECGF; HBGF-1 | NP_000791; NP_001138364; NP_001138406; NP_001138407; NP_001244134-NP_001244142; NP_149127; NP_149128 | AAA51673; AAA51673; AAH32697 |
| | wound healing, tumor growth, fibrosis | fibroblast growth factor 2; heparin-binding growth factor 2; basic FGF | FGF2; bFGF; HBGF-2 | NP_001997 | BAG70135; AAA52531 |
| | oncogenic growth factor, fibrosis | fibroblast growth factor 4; heparin-binding growth factor 4; heparin secretory-transforming protein 1; transforming protein KS3 | FGF4; HST; HST-1; HSTF-1; HBGF-4 | NP_001998; XP-005273904; XP_006718538 | ACJ68447; AAA59473 |
| | epithelial cell-specific growth factor, fibrosis | fibroblast growth factor 7; heparin-binding growth factor 7; keratinocyte growth factor | FGF7; HBGF-7; KGF | NP_002000 | AAA63210; AAB21431 |
| | growth-stimulating effect, fibrosis | fibroblast growth factor 9; glia-activating factor; heparin-binding growth factor 9 | FGF9; GAF; HBGF-9 | NP_002001 | BAA03572; |
| | hormone produced in the ileum in response to bile acid absorption | fibroblast growth factor 19 | FGF19 | NP_005108 | BAA75500 |
| | stimulates stem cells to produce granulocytes (neutrophils, eosinophils, and basophils) and monocytes | granulocyte-macrophage colony-stimulating factor; molgramostim; sargramostim; colony stimulating factor | GM-CSF; CSF2 | NP_000749 | AAA52122 |
| Hematopoiesis ligand | role in hematopoiesis, spermatogenesis and melanogenesis. | stem cell factor; kit ligand; c-Kit ligand; mast cell growth factor | SCF; KL-1; MGF | NP_000890; NP_003985 | AAA85450; AAD22048; AAK92485; AAK92486 |
| Pro-inflammatory markers | overlapping signaling functions with TNF, apoptosis, regulator of angiogenesis | tumor necrosis factor (TNF)-related weak inducer of apoptosis; tumor necrosis factor ligand superfamily member 12 | TWEAK | NP_003800 | AAI04421 |
| | acute phase protein, binds to phosphocholine expressed on the surface of dead or dying cells (and some types of bacteria) to activate the complement system via the C1Q complex | C-reactive protein; | CRP | NP_000558 | AAB59526; AAA52075 |
| | transport of cholesterol to the liver for secretion into the bile, the recruitment of | serum amyloid A | SAA | NP_000322; NP_001171477; NP_954630 | AAA60297; AAA64799 |

-continued

| Functional group | Specific function | Marker name | Abbreviation | NCBI Accession No. | GenBank Accession No. |
|---|---|---|---|---|---|
| | immune cells to inflammatory sites, and the induction of enzymes that degrade extracellular matrix endothelial- and leukocyte-associated transmembrane protein known for its importance in stabilizing cell-cell interactions and facilitating leukocyte endothelial transmigration | intercellular adhesion molecule 1 | ICAM-1; CD54 | NP_000192 | CA30051; AAA52709 |
| | adhesion of lymphocytes, monocytes, eosinophils, and basophils to vascular endothelium | vascular cell adhesion molecule 1 | VCAM-1; CD106 | NP_001069; NP_001186763; NP_542413 | AAA61269 |
| | growth, proliferation, and differentiation of T cells to 'effector' T cells | interleukin-2 | IL-2 | NP_000577 | CAA23827 |
| | mediator of fever and of the acute phase response | interleukin-6 | IL-6 | NP_00591 | AAH15511 |
| | chemotaxis of primarily neutrophils and phagocytosis | interleukin-8 | IL-8 | NP_00575 | AAH13615 |
| | differentiation of naive T cells into Th1 cells | interleukin-12 subunit p70; IL-12A (p35) and IL-12B (p40) | IL-12p70 | NP_000873 (IL-12A) and NP_002178 (IL-12B) | AAA35694 (IL-12A) and AAA35695 (IL-12B) |
| | important mediator of the inflammatory response, cell proliferation, differentiation, and apoptosis. | interleukin-1 beta | IL-1B | NP_000567 | AAA36106 |
| | cytokine critical for innate and adaptive immunity against viral and intracellular bacterial infections and for tumor control | interferon-gamma; IFN-gamma | IFN-γ | NP_000610 | AAH70256 |
| | systemic inflammation, regulation of immune cells | tumor necrosis factor alpha | TNF-α | NP_000585 | AAA61198 |
| Anti-inflammatory marker | pleiotropic effects in immunoregulation and inflammation, downregulation of expression of Th1 cytokines, MHC class II antigens, and co-stimulatory molecules on macrophages, enhancement of B cell survival, proliferation, and antibody production | interleukin-10 | IL-10 | NP_000563 | AAA63207 |
| | bacterial antibodies found in IBD patients, marker used for differential diagnosis of CD vs UC | anti-*Saccharomyces cerevisiae* IgA | ASCAA | | |

Summary of serum markers

| Functional group | Specific function | Marker name | Abbreviation | NCBI Accession No. | GenBank Accession No. |
|---|---|---|---|---|---|
| Serological markers | bacterial antibodies found in IBD patients, marker used for differential diagnosis of CD vs UC | anti-*Saccharomyces cerevisiae* IgG | ASCAG | | |
| | bacterial flagellin that represents systemic evidence of immune reactivity to specific components of the enteric microbiota | bacterial flagellin | CBir1 | | |
| | bacterial flagellin that represents systemic evidence of immune reactivity to specific components of the enteric microbiota | bacterial flagellin | Fla2 | | |
| | bacterial flagellin that represents systemic evidence of immune reactivity to specific components of the enteric microbiota | bacterial flagellin | FLAX | | |
| | major outer-membrane protein, originally isolated from *E. coli*, for which an excessive secretion of antibodies has been reported in CD | outer membrane porin C | OmpC | | |
| | chimeric antibody levels directed towards TNF-α measured right before a new infusion of infliximab | Infliximab trough levels | IFX | | |
| | antibodies generated against infliximab that can cause loss of response | Antibodies to infliximab | ATI | | |

Suitable biomarkers include, but are not limited to, amphiregulin (AREG), heparin-binding EGF-like growth factor (HBEGF), hepatocyte growth factor (HGF), heregulin beta EGF domain (HRGB), betacellulin (BTC), epidermal growth factor (EGF), transforming growth factor alpha (TGFA), fibroblast growth factor 1 (FGF1), fibroblast growth factor 2 (FGF2), fibroblast growth factor 4 (FGF4), fibroblast growth factor 7 (FGF7), fibroblast growth factor 9 (FGF9), fibroblast growth factor 19 (FGF19), granulocyte-macrophage colony-stimulating factor GM-CSF), stem cell factor (SCF), tumor necrosis factor (TNF)-related weak inducer of apoptosis (TWEAK), C-reactive protein (CRP), serum amyloid A (SAA), intercellular adhesion molecule 1 (ICAM-1), vascular cell adhesion molecule 1 (VCAM-1), interleukin-2 (IL-2), interleukin-6 (IL-6), interleukin-8 (IL-8), interleukin-12 subunit p70 (IL-12p70), interleukin-1 beta (IL-B), interferon-gamma (IFN-γ), tumor necrosis factor alpha (TNF-α), interleukin-10 (IL-10), anti-*Saccharomyces cerevisiae* IgA (ASCAA), anti-*Saccharomyces cerevisiae* IgG (ASCAG), bacterial flagellin (CBir-1), bacterial flagellin (Fla2), bacterial flagellin (FlaX), outer membrane porin C (OmpC), Infliximab trough levels (IFX), and Antibodies to infliximab (ATI).

As described herein, in one embodiment, the methods for assessing mucosal healing in a subject include measuring the concentration or level of a set of biomarkers.

In one embodiment, the biomarkers include HGF, BTC, TWEAK and VCAM-1.

In another embodiment, the biomarkers include HGF, BTC, an anti-TNFα drug trough level (e.g., IFX trough levels) and VCAM-1.

In certain aspects, provided herein are methods for predicting mucosal healing or extent in a subject by comparing the levels of HGF, BTC, TWEAK and VCAM-1 detected in a sample to a control value and determining whether the measured levels of the set of markers are associated with mucosal healing. In some embodiments, the comparison includes determining if the HGF level is less than 11.42 CU/ml; the BTC level is greater than 11.44 CU/ml; the TWEAK level is greater than 20.62 CU/ml and the VCAM-1 level is less than 420 μg/ml.

In certain aspects, provided herein are methods for predicting mucosal healing or extent in a subject by comparing the levels of HGF, BTC, IFX trough levels and VCAM-1 detected in a sample to a control value and determining whether the measured levels of the set of markers are associated with mucosal healing. In some embodiments, the comparison includes determining if the HGF level is less than 11.42 CU/ml; the BTC level is greater than 10.3 CU/ml; the IFX trough levels is greater than 5.8 μg/ml and the VCAM-1 level is less than 420 μg/ml.

In certain instances, the presence or level of various markers is detected at the level of mRNA expression with an assay such as, for example, a hybridization assay (e.g., microarray) or an amplification-based assay.

In other instances, the presence or level of various markers is detected at the level of protein expression using, for example, an immunoassay (e.g., ELISA or CEER™), a homogeneous mobility shift assay (HMSA) or an immunohistochemical assay.

Suitable ELISA kits for determining the presence or level of a biomarker in a serum, plasma, saliva, or urine sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

In other instances, the presence or level of various markers is detected using a multiplexed immunoarray, such as a Collaborative Enzyme Enhanced Reactive ImmunoAssay (CEER™), also known as the Collaborative Proximity Immunoassay (COPIA). CEER is described in the following patent documents which are herein incorporated by reference in their entirety for all purposes: PCT Publication Nos. WO 2008/036802, WO 2009/012140, WO 2009/108637, WO 2010/132723, WO 2011/008990, WO 2011/050069; WO 2012/088337; WO 2012/119113; and WO 2013/033623.

One skilled in the art recognizes that an antibody, antibody fragment, immunoconjugate and the like that can specifically bind to (e.g., recognizes) the biomarker polypeptide are useful to detect the level of protein expression of the biomarkers described herein.

In particular embodiments, the presence or level of analytes of interest such as anti-TNF-α drug tough level is detected with a homogeneous mobility shift assay (HMSA) using size exclusion chromatography. These methods and related technology are described in International Patent Publication Nos. WO 2011/056590, WO 2012/054532, WO 2012/154253 and WO 2013/006810, and in U.S. Provisional Application No. 61/683,681, filed Aug. 15, 2012, the disclosures of which are incorporated by reference in their entirety for all purposes.

In certain embodiments, determining the expression (e.g., total) levels of the one or more biomarkers (i.e., analytes) comprises:
(i) incubating (e.g., contacting) a cellular extract produced from a sample with one or a plurality of dilution series of capture antibodies (e.g., capture antibodies specific for one or more analytes) to form a plurality of captured analytes, wherein the capture antibodies are restrained on a solid support (e.g., to transform the analytes present in the cellular extract into complexes of captured analytes comprising the analytes and capture antibodies);
(ii) incubating (e.g., contacting) the plurality of captured analytes with detection antibodies comprising one or a plurality of first and second activation state-independent antibodies specific for the corresponding analytes (e.g., first and second activation state-independent antibodies specific for the one or more analytes) to form a plurality of detectable captured analytes (e.g., to transform the complexes of captured analytes into complexes of detectable captured analytes comprising the captured analytes and detection antibodies), wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;
(iii) incubating (e.g., contacting) the plurality of detectable captured analytes with a second member of the signal amplification pair to generate an amplified signal; and
(iv) detecting the amplified signal generated from the first and second members of the signal amplification pair.

In certain embodiments, the capture antibodies are labeled with a first member of a signal amplification pair in lieu of second activation state-independent antibodies. The facilitating moiety generates an oxidizing agent which channels to and reacts with the first member of the signal amplification pair.

The first activation state-independent antibodies may be directly labeled with the facilitating moiety or indirectly labeled with the facilitating moiety, e.g., via hybridization between an oligonucleotide conjugated to the first activation state-independent antibodies and a complementary oligonucleotide conjugated to the facilitating moiety. Similarly, the second activation state-independent antibodies may be directly labeled with the first member of the signal amplification pair or indirectly labeled, e.g., via binding between a first member of a binding pair conjugated to the second activation state-independent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the first activation state-independent antibodies can be conjugated to a sulfhydryl-activated dextran molecule as described in, e.g., Examples 16-17 of PCT Patent Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, e.g., a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the second activation state-independent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.). Exemplary methods for constructing antibody arrays suitable for use in the invention are described, e.g., in PCT Publication No. WO2009/108637, the disclosure of which is herein incorporated by reference in its entirety for all purposes.

The human hepatocyte growth factor (HGF) polypeptide sequence is set forth in, e.g., NCBI Accession No. NP_000592.3. The human HGF mRNA (coding) sequence is set forth in, e.g., Genbank Accession Nos. NM_000601.4, NM_001010931.1, NM_001010932.1, NM_001010933.1 and NM_001010934.1. One skilled in the art will appreciate that HGF is also known as scatter factor, SF, HPTA and hepatopoietin-A. One of skill will also appreciate that HGF includes all isoform variants.

The human betacellulin (BTC) polypeptide sequence is set forth in, e.g., NCBI Accession No. AAB25452.1. The human BTC mRNA (coding) sequence is set forth in, e.g., Genbank Accession No. NM_001729.2. One skilled in the art will appreciate that BTC includes all isoform variants.

The human TNF-related weak inducer of apoptosis (TWEAK) polypeptide sequence is set forth in, e.g., Genbank Accession No. NP_003800.1. The human TWEAK mRNA (coding) sequence is set forth in, e.g., Genbank Accession No. NM_003809.2. One skilled in the art will appreciate that TWEAK is also known as TNF 12, APO3 ligand, APO3L, DR3LG, and UNQ 181/PRO207.

VCAM-1 (VCAM) is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In one embodiment, it has been determined using multiple logistic regression analyses such as the Bayesian model averaging method that the combination of the 4 biomarkers HGF, BTC, TWEAK and VCAM-1 are highly predictive of mucosal healing in patients with IBD. The model established that the HGF, BTC, TWEAK and VCAM-1 (each individually) has at least a 76.2%, 31.3%, 23.9% and 69.7% probability of being associated with mucosal healing, respectively. Moreover, the combination of all 4 biomarkers results in a better association with mucosal healing than each of the biomarkers alone.

B. Generating an Index Value and a Cumulative Biomarker Score

In some embodiments, the methods of predicting the presence of mucosal healing and/or monitoring the progression or extent of mucosal healing in an individual utilize an empirically derived score (e.g., an index value).

In addition, the methods of selecting an appropriate therapy, optimizing therapeutic efficiency and the like, include the use of the marker score to select, for example, a dose of drug, an appropriate drug, a course or length of therapy, a therapy regimen, or the maintenance of an existing drug or dose. In certain aspects, a derived or measured score can be used for selecting an appropriate therapeutic regimen that promotes mucosal healing.

In certain aspects, each marker in the sample is assigned a index value based upon the concentration and level of the marker relative to a control or a set of controls. In some embodiments, the value is selected from 0 to 4, e.g., 0, 1, 2, 3 or 4; or 1 to 4, e.g., 1, 2, 3, or 4. For example, if the level of a marker is below the level of the lowest control, the marker is assigned a value of 0. If the level of a marker is between the first lowest control and the second control (from low to high), the marker is given a value of 1. If the level of a marker is between the second control and the third control, the marker is given a value of 2. If the level of a marker is between the third control and the fourth control, the marker is given a value of 3. If the level of a marker is between the fourth control and the fifth control (or above the fourth control), the marker is given a value of 4. In certain embodiments, each marker can be assigned a value selected from 0 to 1, 2, 3, 4, 5, 6, 7, 8, 9, 10, 11, 12, 13, 14, 15, 16, 17, 18, 19, 20, 25, 30, or any range therein (e.g., from 1 to 4 or 0 to 4).

In certain aspects, each marker in the sample is assigned an index value based upon the concentration and level of the marker relative to a cut-off value for the same marker. For instance, in some embodiments, the cut-off value for HGF is less than about 11.42 CU/ml; the cut-off value for BTC is greater than about 11.44 CU/ml or greater than about 10.3 CU/ml; the cut-off value for TWEAK is greater than about 20.62 CU/ml; the cut-off value for IFX trough level is 5.8 µg/ml and the cut-off value for VCAM-1 is less than about 420 µg/ml. Thus, the index value for HGF is assigned a value corresponding to mucosal healing, e.g., 4, if the concentration or level of HGF in the sample is less than the cut-off (e.g., 11.42 CU/ml).

In some embodiments, the cut-off value for HGF is <about 11.42 CU/ml, e.g., 0, 1.0, 2.0, 3.0, 4.0, 4.5, 5.0, 6.0, 6.5, 7.0, 8.0, 8.5, 9.0, 9.5, 10.0, 10.5, 11.0, 11.1, 11.2, 11.3, 11.4 CU/ml. In some instances, the cut-off value for HGF is the lower limit of detection for the assay.

In some embodiments, the cut-off value for BTC is >about 11.44 CU/ml, e.g., 11.5, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 CU/ml. In some instances, the cut-off value for BTC is the upper limit of detection for the assay.

In some embodiments, the cut-off value for BTC is >about 10.3 CU/ml, e.g., 10.4, 10.5, 10.6, 10.7, 10.8, 10.9, 11.0, 11.1, 11.2, 11.3, 11.4, 11.5, 11.6, 11.7, 11.8, 11.9, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 CU/ml. In some instances, the cut-off value for BTC is the upper limit of detection for the assay. In some instances, the cut-off value for BTC is the upper limit of detection for the assay.

In some embodiments, the cut-off value for TWEAK is >about 20.62 CU/ml, e.g., 20.7, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 CU/ml. In some instances, the cut-off value for TWEAK is the upper limit of detection for the assay.

In some embodiments, the cut-off value for the trough level of IFX is >about 5.8 µg/ml, e.g., 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 13, 14, or 15 µg/ml. In some instances, the cut-off value is greater than about 20 µg/ml.

In some embodiments, the cut-off value for VCAM-1 is <about 420 µg/ml, e.g., 419, 418, 417, 416, 415, 414, 413, 412, 411, 410, 409, 408, 407, 406, 405, 404, 403, 402, 401, 400, 350, 300, 250, 200, 150, 100, 95, 90, 85, 80, 75, 70, 65, 60, 55, 50, 45, 40, 35, 30, 25, 20, 15, 10, 9, 8, 7, 6, 5, 4, 3, 2 or 1 µg/ml. In some instances, the cut-off value for VCAM-1 is the lower limit of detection for the assay.

In certain aspects, each marker is assigned an index value based upon the quantile level of the marker. In some embodiments, the value is selected from 1 to 4, e.g., 1, 2, 3, or 4. For instance, the values are split into 4 groups ("a quartile") and the markers are assigned a value from 1 to 4 based on its quartile group. In certain embodiments, each marker can be assigned a value selected from 0 to 1, 2, 3, 4, 5, 6, 7, 8, 9, 10, 11, 12, 13, 14, 15, 16, 17, 18, 19, 20, 25, 30, or any range therein (e.g., from 1 to 4). For instance, the values are split into 12 groups and the markers are assigned a value from 0 to 11 based on its quantile group.

In some aspects, the concentration or level of each marker is relative to the level of the same marker in a control patient population, e.g., a population or group of IBD patients that do not exhibit mucosal healing. In other aspects, the concentration or level of each marker is relative to the level of the same marker in a control patient population, e.g., a population or group of IBD patients that exhibit mucosal healing.

In some aspects, the index values for the set of biomarkers is transformed into a cumulative biomarker score. In some embodiments, the cumulative biomarker score is the summation of the index values of the biomarkers including HGF, BTC, TWEAK and VCAM-1.

In some aspects, the index values for the set of biomarkers is transformed into a cumulative biomarker score. In some embodiments, the cumulative biomarker score is the summation of the index values of the biomarkers including HGF, BTC, anti-TNF-α drug trough level and VCAM-1.

In some embodiments, an algorithm is applied to the index values for the biomarkers. In particular, the algorithm allows for the comparison of the index values for HGF and VCAM-1 to the index values of BTC and TWEAK.

In certain instances, the levels of HGF and VCAM-1 are negatively associated with mucosal healing. While on the other hand, the levels of BTC and TWEAK are positively associated with mucosal healing. Thus, in some embodiments, the index values for BTC and TWEAK are inverted in the algorithm used to generate the cumulative biomarker score (see, FIG. 4B).

In some embodiments, the combined biomarker score results in a significant and gradual increased prediction of mucosal healing, whereby measuring all 4 markers (e.g., HGF, BTC, TWEAK and VCAM-1) leads to a prediction of mucosal healing. In some embodiments, the corresponding sensitivity and specificity percentages, positive predictive value (PPV) and negative predictive value (NPV) for the individual marker cut-off points and the biomarker score are as follows for HGF, BTC, TWEAK and VCAM-1: sensitivity percentages of 690%, 32%, 45% and 61%, respectively; specificity percentages of 52%, 67%, 68% and 50%, respectively; PPV of 59%, 46%, 55% and 58%, respectively; and NPV of 62%, 53%, 59% and 53%; respectively. In some embodiments, measuring all 4 markers (e.g., HGF, BTC, TWEAK and VCAM-1) results in a sensitivity and specificity of 81% and 64%, with a PPV of 66% and a NPV of 80%0.

In some embodiments, the biomarker levels of HGF, BTC, TWEAK and VCAM-1 are divided in quartiles for the assessment of mucosal healing. As shown in FIG. 4A, in some embodiments, there is an increased likelihood of mucosal healing if decreasing levels of HGF and VCAM-1 are detected. In some instances, the presence of mucosal healing is associated with levels of HGF and VCAM-1 in quartile 1. In some embodiments, there is an increased likelihood of mucosal healing if increasing levels of BTC and TWEAK are detected. In some instances, the presence of mucosal healing is associated with BTC levels in quartile 3 and TWEAK levels in quartiles 3 or 4. In some embodiments, the cumulative biomarker score is calculated by inverting the quartile scores for BTC and TWEAK, e.g., levels in quartile 1 were given a score of 4, in quartile 2 a score of 3, etc. to obtain a prediction for the likelihood of having mucosal healing. In some embodiments, the cumulative biomarker score is determined such that the prediction for the presence of mucosal healing is associated with biomarker levels in quartile 1.

In certain instances, when TWEAK is being used in the cumulative algorithm score, as shown in FIG. 4B, the cumulative biomarker score of 4-6 indicates mucosal healing, a cumulative biomarker score of 7-10 means partial mucosal healing, a cumulative score of 11-13 means some mucosal healing and a score of 14-16 means no mucosal healing.

In some embodiments, the division of the 4 marker levels into quartiles is shown in FIG. 7A and each serum sample was assigned a score of 1 to 4 based on their designated quartile. The quartile scores were given according to the positive or negative association with healing. Therefore, lower levels of HGF and VCAM-1 were given a score of 4, whereas lower levels of BTC and IFX trough were given a score of 1. In this embodiment, an index of 4 is associated with mucosal healing.

As shown in FIG. 7C, a significant gradually increasing probability of mucosal healing was found for decreasing levels of HGF (linear trend test, p=0.036) and VCAM-1 (linear trend test, p=0.029), with the highest probabilities of healing associated to levels in quartiles 2 and 1 (42% and 50%), respectively. In contrast, the probability of mucosal healing was higher for increased levels of BTC (linear trend test, p=0.007) and IFX trough (linear trend test, p=0.035). For BTC, a higher probability of healing was found in quartiles 2 and 3 (59% and 57%) as compared to quartile 4

(40%). In the case of IFX trough levels, a gradually increasing mucosal healing probability was found with the highest probability for levels in quartile 4 (51%). The sum of all quartile scores was then calculated (FIG. 7C) and divided into quartiles again. A positive test result for all 4 markers (score 4) was observed in 67% of the samples matched to mucosal healing (linear trend test, p<0.001) (FIG. 7C). ROC determined an AUC of 0.702 (0.623-0.781) for using the quartile of the sum of quartile scores. In some other embodiments, the cumulative biomarker score of 14-16 indicates mucosal healing, a cumulative biomarker score of 11-13 means partial mucosal healing, a cumulative score of 7-10 means some mucosal healing and a score of 4-6 means no mucosal healing.

C. Statistical Algorithms for Mucosal Healing

In certain aspects, the present invention provides a method that incorporates the index value described herein to improve the sensitivity, specificity, and/or accuracy of predicting mucosal healing in a subject with IBD, including Crohn's disease and ulcerative colitis.

In some aspects, the present invention provides methods for predicting the likelihood of mucosal healing for a subject by applying a statistical algorithm to the index value to generate a mucosal healing measurement, such as a cumulative biomarker score.

The term "statistical analysis" or "statistical algorithm" or "statistical process" includes any of a variety of statistical methods and models used to determine relationships between variables. In the present invention, the variables are the presence and/or level of at least one marker of interest. Any number of markers can be analyzed using a statistical analysis described herein. For example, the presence or level of 1, 2, 3, 4, or more markers can be included in a statistical analysis. In one embodiment, logistic regression is used. In another embodiment, linear regression is used. In yet another embodiment, ordinary least squares regression or unconditional logistic regression is used.

In some embodiments, the statistical analyses of the present invention comprise a quantile measurement of one or more markers, e.g., within a given population, as a variable. Quantiles are a set of "cut-off values" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In some embodiments, the statistical analyses of the present invention comprise one or more univariate analyses including, but not limited to, Mann-Whitney U test, receiver operating characteristic (ROC) analyses and univariate binary logistic regression. In some embodiments, multiple logistic regression analysis is performed to select the best set of biomarkers associated with mucosal healing based on the Bayesian information criterion (BIC) (R-package: BMA). In some embodiments, internal validation is performed with bootstrapping. In some instances, statistical analysis is performed in the statistical software platforms SPSS (IBM Corp., Armonk, N.Y.) and R.

Detailed descriptions of ROC analyses are found in, e.g., Zweig, M. H., and G. Campbell, *Clinical Chemistry*, 1993, 39:4, 561-577 and Woods, K., and K. W. Bowyer, *IEEE Transactions on Medical Imaging*, 1997, 16, 329-337. Detailed descriptions of Bayesian models are found in, e.g., Becker, B., R. Kohavi, and D. Sommerfield. 2001. Visualizing the Simple Bayesian Classifier. In: Information Visualization in Data Mining and Knowledge Discovery, U. Fayyad, G. Grinstein, and A. Wierse, eds. San Francisco: Morgan Kaufmann Publishers and Natarajan, R., and E. Pednault. 2001. Using Simulated Pseudo Data to Speed Up Statistical Predictive Modeling from Massive Data Sets. In: SIAM First International Conference on Data Mining.

D. Biomarker Index Scores Correspond to Endoscopic Measurement Scores

In certain aspects, the present invention provides a method for determining an endoscopic measurement score for an individual by correlating the cumulative biomarker score described herein to the measurement score. In some embodiments, the cumulative biomarker score is a surrogate for the endoscopic measurment score, and optionally it can be determined using a look-up table.

The Crohn's Disease Endoscopic Index of Severity (CDEIS) Score, an endoscopic measurement scoring system, is an assessment of a subject's segmental rectocolonic frequency deep ulcerations and superficial ulcerations and the presence of ulcerated stenosis and nonulcerated stenosis in the terminal ileum, ascending colon, transverse colon, descending and sigmoid colon and the rectum (See, e.g., Khanna et al., *Inflamm Bowel Dis*, 2014, 20(10):1850-1861). The scales are the set as the following: the presence of deep ulceration ranges from 0 for absent to 12 for present; the presence of mucosal superficial ulceration ranges from 0 for absent to 6 for present; the extent of surface involvement in the disease ranges from 0 for absent to 10 for present; the extent of ulcerated surface ranges from 0 for absent to 10 for present; the presence of ulcerated stenosis from 0 for absent to 3 for present; and the presence of non-ulcerated stenosis from 0 for absent to 3 for present, for each segment. The CDEIS score ranges from 0 to 44 as the sum of all the variables in all the segments, with a higher score indicating more severe disease. In some embodiments, a decrease in CDEIS score of >5 points corresponds to disease response to therapy; a CDEIS score of ≥6 is equated to disease remission; a CDEIS score of ≥3 corresponds to complete remission. In other embodiments, CDEIS scores of less than 5, 5-15, and greater than 15 represent mild, moderate, and severe disease, respectively.

The Simple Endoscopic Score in Crohn's Disease (SES-CD), another endoscopic measurement scoring system, includes evaluating ulcer size, the proportion of ulcerated surface, the proportion of the surface area affected by any disease lesion, and stenosis. These variables are scored from 0 to 3, in the ileum, right colon, transverse colon, left colon, and rectum (See, e.g., Khanna et al., *Inflamm Bowel Dis*, 2014, 20(10):1850-1861). The total SES-CD is calculated as the sum of all the scores for the variables in all the gastrointestinal segments.

In some embodiments, mucosal healing determined to be present in a subject if there is an at least 50% decrease in CDEIS or SES-CD score from baseline (e.g., time point 1). Alternatively, if a decrease of less than 50% in CDEIS or SES-CD score from baseline or an increase in CDEIS or SES-CD score from baseline is detected, it is determined that the subject is not undergoing or has not undergone mucosal healing.

In some embodiments, the cumulative biomarker score of 4, as determined from the biomarker values for, e.g., VCAM-1, HGF, BTC and TWEAK, corresponds to a SES-CD score of 0-4, e.g., 0, 1, 2, 3 or 4, or a CDEIS score of about less than 6, e.g., 6, 5, 4, 3, 2, 1, or 0. In some instances, the cumulative score of 4-6, corresponds to a SES-CD score of 0-4, e.g., 0, 1, 2, 3 or 4, a CDEIS score of about less than 6, e.g., 6, 5, 4, 3, 2, 1, or 0, or mucosal healing. In other embodiments, a cumulative score of 14-16 corresponds to a CDEIS score of >6, e.g., 7, 8, 9, 10, 11, 12, 13, 14, 15, 16, 17, 18, 19, 20, 21, 23, 24, 25, 26, 27, 28, 29, 30, 31, 32, 33, 34, 35, 36, 37, 38, 39, 40, 41, 42, 43, or 44, severe disease, or the absence of mucosal healing.

In some embodiments, the cumulative biomarker score of 4, as determined from the biomarker values for, e.g., VCAM-1, HGF, BTC and TWEAK, predicts that the subject has or will have an at least 50% decrease in CDEIS or SES-CD score from baseline (e.g., time point 1). In other embodiments, the cumulative biomarker score of 4-6 indicates that the subject has or will have an at least 50% decrease in CDEIS or SES-CD score from baseline. In some instances, the cumulative biomarker score of 4-6 indicates mucosal healing. In other embodiments, a cumulative biomarker score of 7-16 corresponds to a less than 50% decrease in CDEIS or SES-CD score from baseline. In yet other embodiments, a cumulative score of 14-16 represents no change or an increase in CDEIS or SES-CD score from baseline. In some embodiments, a cumulative biomarker score of 7-10 corresponds to an at least 25% decrease in CDEIS or SES-CD score from baseline. In other embodiments, a cumulative biomarker score of 11-13 corresponds to an about 1% to less than 25% decrease in CDEIS or SES-CD score from baseline.

In some embodiments, the cumulative biomarker score of 16, as determined from the biomarker values for, e.g., VCAM-1, HGF, BTC and anti-TNFα drug trough, corresponds to a SES-CD score of 0-4, e.g., 0, 1, 2, 3 or 4, or a CDEIS score of about less than 6, e.g., 6, 5, 4, 3, 2, 1, or 0. In some instances, the cumulative score of 4-6, corresponds to a SES-CD score of 0-4, e.g., 0, 1, 2, 3 or 4, a CDEIS score of about less than 6, e.g., 6, 5, 4, 3, 2, 1, or 0, or mucosal healing. In other embodiments, a cumulative score of 4-6 corresponds to a CDEIS score of >6, e.g., 7, 8, 9, 10, 11, 12, 13, 14, 15, 16, 17, 18, 19, 20, 21, 23, 24, 25, 26, 27, 28, 29, 30, 31, 32, 33, 34, 35, 36, 37, 38, 39, 40, 41, 42, 43, or 44, severe disease or the absence of mucosal healing.

In some embodiments, the cumulative biomarker score of 16, as determined from the biomarker values for, e.g., VCAM-1, HGF, BTC and anti-TNFα drug trough, predicts that the subject has or will have an at least 50% decrease in CDEIS or SES-CD score from baseline (e.g., time point 1). In other embodiments, the cumulative biomarker score of 14-16 indicates that the subject has or will have an at least 50% decrease in CDEIS or SES-CD score from baseline. In some instances, the cumulative biomarker score of 14-16 indicates mucosal healing. In other embodiments, a cumulative biomarker score of 14-4 corresponds to a less than 50% decrease or an increase in CDEIS or SES-CD score from baseline. In yet other embodiments, a cumulative score of 4-6 represents no change or an increase in CDEIS or SES-CD score from baseline. In some embodiments, a cumulative biomarker score of 11-13 corresponds to an at least 25% decrease in CDEIS or SES-CD score from baseline. In other embodiments, a cumulative biomarker score of 7-10 corresponds to an about 1% to less than 25% decrease in CDEIS or SES-CD score from baseline. In other embodiments, a cumulative biomarker score of 4-6 corresponds to a less than 1% decrease, no change or an increase in CDEIS or SES-CD score from baseline or the absence of mucosal healing.

IV. Examples

The following example is offered to illustrate, but not to limit, the claimed invention.

Example 1

This example illustrates a method for predicting the presence of mucosal healing in a patient with IBD including Crohn's disease or ulcerative colitis. The method includes measuring the levels of four biomarkers including HGF, BTC, TWEAK and VCAM-1 in a serum sample from the patient; comparing the levels to that of a control, and using one or more statistical algorithms to determine whether the patient has an increased likelihood of having mucosal healing.

Anti-TNF antibodies have introduced new therapeutic goals in Crohn's disease (CD) such as mucosal healing and improvement of quality of life. The current standard for assessing mucosal healing is still endoscopy. However, frequent assessments are costly and uncomfortable to the patient. Non-invasive, accurate surrogate serum markers would therefore be welcomed.

Thirty-six markers were measured in 181 serum samples from 119 CD patients undergoing serial endoscopies before and during infliximab therapy with the use of CEER™ (Prometheus Laboratories. San Diego, Calif.) or homogenous mobility shift assays. Serum samples were collected at the time of the endoscopies and levels were correlated with healing status. The studied markers included repair factors, pro- and anti-inflammatory markers and the IBD SGI serology panel, as well as infliximab trough levels and antibodies to infliximab. Marker levels were analyzed for association with healing status using appropriate techniques in SPSS and R.

Of the 119 CD patients, 54% showed complete healing after IFX, whereas 46% patients never showed mucosal healing. Univariate analyses indicated several markers that were significantly associated with mucosal healing ($p<0.1$). Multiple logistic regression analysis retained hepatocyte growth factor (HGF) [0.86 (0.79-0.94), p=0.001], betacellulin (BTC) [1.24 (1.07-1.43), p=0.003], tumor necrosis factor-related weak inducer of apoptosis (TWEAK) [1.04 (1.01-1.07), p=0.014] and vascular cell adhesion molecule 1 (VCAM-1) [0.93 (0.87-0.98), p=0.012] as independent markers associated with mucosal healing. The results remained significant after bootstrapping. A cumulative biomarker score combining the 4 markers (HGF<11.42 CU/ml, BTC>11.44 CU/ml, TWEAK>20.62 CU/ml and VCAM<420 g/ml) resulted in a significant increased prediction of mucosal healing (83%, p<0.001).

The inventors have advantageously identified a biomarker panel that includes four serum makers which are significantly associated with endoscopic healing (e.g., mucosal healing) in response to infliximab. The biomarker panel provides a non-invasive method for predicting mucosal healing in a patient with inflammatory bowel disease, such as Crohn's disease or ulcerative colitis.

A. Introduction

In this study, 36 serum markers with different functions related to the pathogenesis or chronic course of IBD were evaluated for their role in the assessment of mucosal healing. All the serum markers and their functional properties are summarized in Table 1 below.

TABLE 1

Summary of serum markers.

| Functional group | Specific function | Marker name | Abbreviation |
|---|---|---|---|
| Growth and repair factors | member of the epidermal growth factor family | amphiregulin | AREG |
| | member of the epidermal growth factor family | heparin-binding EGF-like growth factor | HBEGF |
| | cellular growth, motility and morphogenic factor - mucosal repair and fibrosis | hepatocyte growth factor | HGF |
| | member of the epidermal growth factor family | heregulin beta EGF domain | HRGB |
| | member of the epidermal growth factor family -mucosal repair | betacellulin | BTC |
| | cell growth, proliferation, and differentiation | epidermal growth factor | EGF |
| | cell proliferation, differentiation and development | transforming growth factor alpha | TGFA |
| | modifier of endothelial cell migration and proliferation, angiogenic factor, fibrosis | fibroblast growth factor 1 | FGF1 |
| | wound healing, tumor growth, fibrosis | fibroblast growth factor 2 | FGF2 |
| | oncogenic growth factor, fibrosis | fibroblast growth factor 4 | FGF4 |
| | epithelial cell-specific growth factor, fibrosis | fibroblast growth factor 7 | FGF7 |
| | growth-stimulating effect, fibrosis | fibroblast growth factor 9 | FGF9 |
| | hormone produced in the ileum in response to bile acid absorption | fibroblast growth factor 19 | FGF19 |
| | stimulates stem cells to produce granulocytes (neutrophils, eosinophils, and basophils) and monocytes | granulocyte-macrophage colony-stimulating factor | GM-CSF |
| Hematopoiesis ligand | role in hematopoiesis, spermatogenesis and melanogenesis. | stem cell factor | SCF |
| Pro-inflammatory markers | overlapping signaling functions with TNF, apoptosis, regulator of angiogenesis | tumor necrosis factor (TNF)-related weak inducer of apoptosis | TWEAK |
| | acute phase protein, binds to phosphocholine expressed on the surface of dead or dying cells (and some types of bacteria) to activate the complement system via the C1Q complex | C-reactive protein | CRP |
| | transport of cholesterol to the liver for secretion into the bile, the recruitment of immune cells to inflammatory sites, and the induction of enzymes that degrade extracellular matrix | serum amyloid A | SAA |
| | endothelial- and leukocyte-associated transmembrane protein known for its importance in stabilizing cell-cell interactions and facilitating leukocyte endothelial transmigration | intercellular adhesion molecule 1 | ICAM-1 |
| | adhesion of lymphocytes, monocytes, eosinophils, and basophils to vascular endothelium | vascular cell adhesion molecule 1 | VCAM-1 |
| | growth, proliferation, and differentiation of T cells to 'effector' T cells | interleukin-2 | IL-2 |
| | mediator of fever and of the acute phase response | interleukin-6 | IL-6 |
| | chemotaxis of primarily neutrophils and phagocytosis | interleukin-8 | IL-8 |
| | differentiation of naive T cells into Th1 cells | interleukin-12 subunit p70 | IL-12p70 |
| | important mediator of the inflammatory response, cell proliferation, differentiation, and apoptosis. | interleukin-1 beta | IL-1B |
| | cytokine critical for innate and adaptive immunity against viral and intracellular bacterial infections and for tumor control | interferon-gamma | IFN-γ |
| | systemic inflammation, regulation of immune cells | tumor necrosis factor alpha | TNF-α |

TABLE 1-continued

Summary of serum markers.

| Functional group | Specific function | Marker name | Abbreviation |
|---|---|---|---|
| anti-inflammatory marker | pleiotropic effects in immunoregulation and inflammation, downregulation of expression of Th1 cytokines, MHC class II antigens, and co-stimulatory molecules on macrophages, enhancement of B cell survival, proliferation, and antibody production | interleukin-10 | IL-10 |
| Serological markers | bacterial antibodies found in IBD patients, marker used for differential diagnosis of CD vs UC | anti-*Saccharomyces cerevisiae* IgA | ASCAA |
| | bacterial antibodies found in IBD patients, marker used for differential diagnosis of CD vs UC | anti-*Saccharomyces cerevisiae* IgG | ASCAG |
| | bacterial flagellin that represents systemic evidence of immune reactivity to specific components of the enteric microbiota | bacterial flagellin | CBir1 |
| | bacterial flagellin that represents systemic evidence of immune reactivity to specific components of the enteric microbiota | bacterial flagellin | Fla2 |
| | bacterial flagellin that represents systemic evidence of immune reactivity to specific components of the enteric microbiota | bacterial flagellin | FLAX |
| | major outer-membrane protein, originally isolated from *E. coli*, for which an excessive secretion of antibodies has been reported in CD | outer membrane porin C | OmpC |
| | chimeric antibody levels directed towards TNF-α measured right before a new infusion of infliximab | Infliximab trough levels | IFX |
| | antibodies generated against infliximab that can cause loss of response | Antibodies to infliximab | ATI |

The studied markers included several growth and repair factors, including 5 members of the epidermal growth factor family [amphiregulin (AREG); heparin-binding EGF-like growth factor (HBEGF), heregulin beta EGF domain (HRGB), betacellulin (BTC) and epidermal growth factor (EGF)], hepatocyte growth factor (HGF), transforming growth factor alpha (TGFA), granulocyte-macrophage colony-stimulating factor (GM-CSF) and 6 members of the fibroblast growth factor family (FGF) [FGF1, 2, 4, 7, 9 and 19]. Several of these markers have been associated with tissue repair and mucosal healing in IBD (Beck et al., *Inflamm. Bowel Dis.*, 1999, 5:44-60; Krishnan et al., *Inflamm. Bowel Dis.*, 2011, 17:410-422; Matsuno et al., *Res Commun. Mol. Pathol. Pharmacol.*, 1997, 97:25-37; Homi et al., *Growth Factors*, 2000, 18:79-91; Egea et al., *Expert Rev. Gastroenterol. Hepatol.*, 2010, 4:723-731; Houchen et al., *Inflamm Bowel Dis.*, 2003, 9:133; Diechgraefe et al., *Ann. N.Y. Acad. Sci.*, 2006, 1072:300-306; Van Assche et al., *Gut*, 2006, 55:1568-1574).

A range of pro-inflammatory markers was also studied, including several interleukins [(IL), IL-1beta, IL-2, IL-6, IL-8 and IL12p70], acute phase proteins [C-reactive protein (CRP) and serum amyloid A (SAA)], cell adhesion molecules [vascular cell adhesion molecule 1 (VCAM-1) and intercellular adhesion molecule 1 (ICAM-1)], tumor necrosis factor (TNF)-related weak inducer of apoptosis (TWEAK), interferon-gamma (IFN-γ) and TNF-α. Moreover, IL-10 as anti-inflammatory marker was also investigated. Inflammatory proteins play a crucial role in the pathogenesis of IBD and in the persistence of inflammation and tissue injury. Several cytokines play key roles in mediating acute inflammatory reactions, namely IL-1, TNF-α, IL-6 and IL-8. The cytokines known to mediate chronic inflammatory processes can be divided into those participating in humoral inflammation (IL-6 and IL-10) and those contributing to cellular inflammation (IL-1, IL-2, IL-10, IL-12, IFN-γ and TNF-α). Directly blocking T-helper cell 1 (Th1) cytokines, such as IL-2 or IFN-γ, has not been proven to be successful in IBD clinical trials (13, 14) (Van Assche et al., *Gut*, 2006, 55:1568-1574; Reinisch et al., *Gut*, 2006, 55:1138-1144). However, blocking the migration of activated leukocytes responsible for on-site cytokine release into the inflamed tissue by specific antibodies such as vedolizumab (an α4β7 integrin antibody), seems highly effective (Gerner et al., *Dig. Dis.*, 2013, 31:328-335; Sandborn et al., *N. Engl J Med.*, 2013, 369:711-721). The dual role of IL-6 in both cell-mediated and humoral immunity underlines its key role in the modulation of the inflammatory response. IL-6 is therefore considered as a strategic bridge between the innate and the adaptive immune system, and is therefore supposed to be an ideal target for anti-inflammatory treatment (Allocca et al., *Curr. Drug Targets*, 2013, 14:1508-1521). Several studies have been performed in both animal models of colitis (Yamamoto et al., *J. Immunol*, 2000, 164:4878-4882; Atreya et al., *Nature Med.*, 2000, 6:583-588; Mitsuyama et al., *Gut*, 2006, 55:1263-1269) and patients with IBD (Gross et al., *Gastroenterology* 1992, 102:514-519; Nikolaus et al., *Gut*, 1998, 42:470-476), identifying this crucial cytokine in the pathophysiology of IBD. Moreover, high levels of IL-6 were found to be predictive of relapse in quiescent CD patients (Louis et al., Eur. J. Gastroenterol. Hepatol., 1997, 9:939-944). The most successful treatment so far has been blocking TNF-α with a chimeric monoclonal antibody (infliximab, Remicade™). This has had a major impact on clinical practice and led to a readjustment of treatment goals in CD (Danese et al., *Aliment. Pharmacol. Ther.*, 2011, 33:857-869; Schnitzler et al., *Inflamm Bowel Dis.*, 2009, 15:1295-1301).

A serology panel consisting of six bacterial markers was also measured. The panel included anti-*Saccharomyces cerevisiae* IgA (ASCAA), anti-*Saccharomyces cerevisiae* IgG (ASCAG), bacterial flagellin (CBir1), bacterial flagellin (Fla2), bacterial flagellin (FLAX) and outer membrane porin C (OmpC). ASCA is a marker used for diagnosis of CD. Moreover, in combination with perinuclear anti-neutrophil cytoplasmic autoantibodies (pANCA) it can be helpful for differentiation between UC and CD (Quinton et al., *Gut*, 1998, 42:788-791; Ferrante et al., *Gut*, 2007, 56:1394-1403). Antibodies against the bacterial flagellin CBir have also been found in CD patients, and are associated with perforating disease and the need for small-bowel surgery (Targan et al., *Gastroenterology*, 2005, 128:2020-2028). The flagellins Fla-2 and FLAX are 2 relatively new described flagellins and are associated with complicated CD (Schoepfer et al., *Inflamm. Bowel Dis.*, 2009, 15:1358-1367). OmpC is a major outer-membrane protein, originally isolated from *E. coli*, for which an excessive secretion of antibodies has been reported in CD (Peyrin et al., *Injlamm. Bowel Dis.*, 2007, 13:1561-1566).

Moreover, a hematopoiesis ligand [stem cell factor (SCF)] was measured. SCF, also known as c-kit ligand, is thought to play a role in the regulation of mediator release in human intestinal mast cells (Bischoff et al., *Gut*, 1996, 38:104-114). The enhancement of mediator release by cytokines may be of particular relevance in the pathogenesis of IBD.

Finally, infliximab (IFX) trough levels and antibodies to infliximab (ATI) levels were measured. Infliximab trough levels were associated with a higher rate of clinical remission for CD patients with a detectable infliximab trough level compared to CD patients with undetectable trough levels. A detectable infliximab trough level was also associated with a lower CRP and a higher rate of endoscopic improvement (Maser et al., *Clin Gastroenterol Hepatol.*, 2006, 4:1248-1254). Infliximab can elicit an immunogenic response which can lead to the development of ATI. Approximately 6-17% of the patients treated with scheduled infliximab develop ATI (Hanauer et al., *Clin. Gastroenterol. Hepatol.*, 2004, 2:542-553; Sands et al., *N. Engl. J. Med.* 2004, 350:876-885). Formation of ATI was associated with an increased risk of infusion reactions and a reduced duration of response to treatment (Baert et al., *N. Engl. J. Med.*, 2003, 348:601-608). However, ATI may be transient and might not always lead to a worse clinical outcome (Vande Casteele et al., *Am J Gastroenterol.*, 2013, 108:962-971).

In this study, 36 serum markers were measured and correlated to mucosal healing status at time of blood sampling. Some patients gave serial serum samples taken around the time of follow-up endoscopy after initiation of infliximab therapy. All serum markers were evaluated for their association with mucosal healing. Finally, it was investigated whether measuring a combination of serum markers, which were identified as independent markers associated with mucosal healing, would improve the successful assessment of mucosal healing.

B. Methods

Patient sampling. In this retrospective study, serum samples were collected from 119 CD patients who started infliximab and who underwent serial endoscopies (before and during infliximab). The baseline characteristics of the CD patients are shown in Table 2. Of the CD patients included in the study, 55 patients had no healing at time of serum sampling and 64 patients had complete or partial healing at time of sampling.

TABLE 2

CD patient characteristics.

|  | No healing (n = 55) | Mucosal healing (n = 64) | p-value |
|---|---|---|---|
| CD patient characteristics |  |  |  |
| male/female (%) | 45/55 | 52/48 | 0.58[b] |
| median (IQR) age at sampling (years) | 45 (35-58) | 44 (36-55) | 0.54[a] |
| median (IQR) age at diagnosis (years) | 23 (16-30) | 22 (17-32) | 0.98[a] |
| Ileal involvement at first infliximab (%)* | 58 | 50 | 0.45[b] |
| Colonic involvement at first infliximab (%) | 80 | 88 | 0.32[b] |
| location of disease at first infliximab (Vienna classification) (%) |  |  | 0.08[c] |
| 1 | 15 | 8 |  |
| 2 | 30 | 25 |  |
| 3 | 55 | 58 |  |
| 4 | 0 | 9 |  |
| anal involvement (%) | 53 | 52 | 1[b] |
| surgery prior to first colonoscopy (%) | 64 | 55 | 0.35[b] |
| active smoking (%)† | 49 | 43 | 0.66[b] |
| concomitant medication (%) |  |  |  |
| Azathioprine (AZA) | 27 | 17 | 0.27[b] |
| Methotrexate (MTX) | 4 | 3 | 1[b] |
| Steroids | 11 | 17 | 0.43[b] |

Abbreviations: IQR, interquartile range
[a]Mann-Whitney U test
[b]Fisher-exact test
[c]Chi-square test
*<10% missing values
†30.4% missing values The serum samples were available through the existing VLECC biobank and were matched to the time of endoscopy. Serum levels were correlated with mucosal healing status that was defined by an IBD-specialist. Complete mucosal healing was defined as absence of ulcerations at follow-up endoscopy in patients who had ulcerations present at baseline ileocolonoscopy and partial mucosal healing was defined as clear endoscopic improvement, but with still ulceration present. In case of no endoscopic improvement or endoscopic worsening patients were classified as non-healers. In total, 181 serum samples were measured belonging to 42 patients that gave one serum sample, 49 patients that gave two serial serum samples and 12 patients that gave 3 serial serum samples. From all individuals a written informed consent was obtained.

Serum marker level measurements. CEER™, a proprietary highly sensitive protein micro-array developed by Prometheus Laboratories (San Diego, Calif.), was used for serum level measurements of AREG, EREG, HBEGF, HGF, HRGB, BTC, EGF, TGFA, FGF1, FGF2, FGF4, FGF7, FGF9, FGF19, SCF, TWEAK, PDGFB and VEGFA. ASCAA, ASCAG, CBir1, Fla2, FLAX and OmpC were measured with the PROMETHEUS® IBD sgi Diagnostic™ test. Infliximab trough levels, antibodies to infliximab levels, CRP, ICAM-1, SAA, VCAM-1, IL-2, IL-8, IL-12p70, IL-1B, GM-CSF, IFN-γ, IL-6, IL-10 and TNF-α were measured with homogeneous mobility shift (HMSA) assays. The detection limits of the tests per marker are listed in Table 3

TABLE 3

Detection limits of all serum markers measured by CEER ™ or Homogeneous Mobility Shift Assay (HMSA).

|  | Marker | Lower | Upper |
|---|---|---|---|
| CEER (CU/ml) | AREG | 1.25 | 10 |
|  | EREG | 50 | 400 |
|  | HBEGF | 1.25 | 10 |
|  | HGF | 4 | 32 |
|  | HRG | 6 | 48 |
|  | BTC | 8 | 64 |
|  | EGF | 0.624 | 40 |
|  | TGFA | 0.6 | 4.8 |
|  | FGF1 | 6 | 48 |
|  | FGF2 | 3 | 24 |
|  | FGF4 | 5 | 40 |
|  | FGF7 | 0.95 | 7.6 |
|  | FGF9 | 3 | 24 |
|  | FGF19 | 12.5 | 100 |
|  | SCF | 1.25 | 10 |
|  | TWEAK | 2.5 | 20 |
|  | PDGFB | 15 | 120 |
|  | VEGFA | 2.5 | 20 |
| HMSA (μg/ml) | CRP | 3.1 | 200 |
|  | ICAM-1 | 3.1 | 200 |
|  | SAA | 3.1 | 200 |
|  | VCAM-1 | 3.1 | 200 |
|  | IL-2 | 3.1 | 200 |
|  | IL-8 | 3.1 | 200 |
|  | IL-12p70 | 3.1 | 200 |
|  | IL-1B | 3.1 | 200 |
|  | GM-CSF | 3.1 | 200 |
|  | IFN-γ | 3.1 | 200 |
|  | IL-6 | 3.1 | 200 |

TABLE 3-continued

Detection limits of all serum markers measured by CEER ™ or Homogeneous Mobility Shift Assay (HMSA).

| Marker | Lower | Upper |
|---|---|---|
| IL-10 | 3.1 | 200 |
| TNF-α | 3.1 | 200 |
| ASCAA | 3.1 | 200 |
| ASCAG | 3.1 | 200 |
| CBir1 | 3.1 | 200 |
| Fla2 | 3.1 | 200 |
| FLAX | 3.1 | 200 |
| OmpC | 3.1 | 200 |
| IFX | 0.98 | 34 |
| ATI | 0.98 | 34 |

Missing values and outliers. Markers that had more than 20 percent missing data were excluded from further analyses (this was the case for PDGFB, VEGFA and EREG). In the remaining dataset, missing values were replaced with the median of the series per marker with the use of simple imputation in SPSS. To detect outliers in the dataset, Cook's distance values that exceeded 1 and Leverage values that were higher than 0.5 were assessed. This resulted in the exclusion of 5 serum samples (belonging to 2 CD patients) that were identified as outliers.

Statistical Analysis.

Several univariate analyses were performed to investigate the individual association with mucosal healing for each marker. These analyses included Mann-Whitney U test, Receiver operating characteristic (ROC) analyses and univariate binary logistic regression. Spearman and Kendall's tau correlation analyses were performed to detect co-linearity. Correlation factors above 0.7 were considered significant. Multiple logistic regression analysis was performed to select the best subset of markers associated with mucosal healing based on the Bayesian information criterion (BIC) (R-package: BMA). Internal validation was performed with bootstrapping (n=1000). Statistical analysis was performed in SPSS and R and p-values <0.05 were considered significant, unless otherwise stated in the text.

C. Results i. Univariate Analyses Identified Several Markers Associated with Mucosal Healing From the 119 CD patients, 55 patients showed no mucosal healing, whereas 64 patients showed complete or partial mucosal healing. Comparison of marker levels between serum samples taken at the time of no healing and mucosal healing determined 14 markers (HGF, BTC, FGF2, TWEAK, IFX trough levels, CRP, ICAM-1, SAA, VCAM-1, IL-2, IL-8, IFN-γ, IL-6 and IL-10) that were significantly associated with mucosal healing (Mann-Whitney U test, p<0.1) (Table 4). For most of these markers, lower levels were associated with mucosal healing, however; for BTC, FGF2 and TWEAK and also for IFX trough levels, higher levels were significantly associated with mucosal healing.

TABLE 4

Serum marker characteristics.

| Marker name | Marker | Median (IQR) no healing (n = 97) | Median (IQR) mucosal healing (n = 84) | p-value[a] |
|---|---|---|---|---|
| amphiregulin | AREG | 1.25 (1.25-6.55) | 1.99 (1.25-6.74) | 0.40 |
| heparin-binding EGF-like growth factor | HBEGF | 4.26 (3.68-6.10) | 4.26 (3.39-6.30) | 0.62 |
| hepatocyte growth factor | HGF | 12.76 (10.67-16.82) | 11.36 (9.14-12.72) | 0.0004*** |
| heregulin beta EGF domain | HRGB | 6.00 (6.00-10.17) | 6.00 (6.00-15.00) | 0.47 |
| betacellulin | BTC | 8.00 (8.00-12.06) | 10.61 (8.00-11.97) | 0.078† |

TABLE 4-continued

Serum marker characteristics.

| Marker name | Marker | Median (IQR) no healing (n = 97) | Median (IQR) mucosal healing (n = 84) | p-value$^a$ |
|---|---|---|---|---|
| epidermal growth factor | EGF | 5.02 (3.09-8.57) | 4.73 (2.78-7.53) | 0.34 |
| transforming growth factor alpha | TGFA | 1.13 (0.93-1.49) | 1.09 (0.91-1.49) | 0.56 |
| fibroblast growth factor 1 | FGF1 | 9.84 (6.94-13.02) | 10.19 (8.31-13.84) | 0.26 |
| fibroblast growth factor 2 | FGF2 | 3.00 (3.00-3.00) | 3.00 (3.00-4.77) | 0.038* |
| fibroblast growth factor 4 | FGF4 | 6.90 (5.00-9.59) | 7.15 (5.00-10.03) | 0.50 |
| fibroblast growth factor 7 | FGF7 | 1.33 (0.95-1.63) | 1.33 (0.95-1.73) | 0.31 |
| fibroblast growth factor 9 | FGF9 | 3.00 (3.00-5.01) | 3.45 (3.00-4.92) | 0.47 |
| fibroblast growth factor 19 | FGF19 | 12.50 (12.50-12.50) | 12.50 (12.50-12.50) | 0.94 |
| stem cell factor | SCF | 1.60 (1.25-2.42) | 1.67 (1.25-2.33) | 0.56 |
| tumor necrosis factor (TNF)-related weak inducer of apoptosis | TWEAK | 14.99 (2.50-22.93) | 19.93 (13.24-26.81) | 0.005** |
| Infliximab trough levels | IFX | 0.98 (0.98-8.26) | 4.10 (0.98-12.24) | 0.015* |
| Antibodies to infliximab | ATI | 0.98 (0.98-0.98) | 0.98 (0.98-0.98) | 0.83 |
| C-reactive protein | CRP | 0.94 (0.28-3.33) | 0.40 (0.12-1.10) | 0.0007*** |
| intercellular adhesion molecule 1 | ICAM-1 | 3.15 (2.15-5.26) | 2.74 (2.09-3.76) | 0.03* |
| serum amyloid A | SAA | 9.03 (2.71-25.70) | 2.91 (0.10-6.58) | <0.0001*** |
| vascular cell adhesion molecule 1 | VCAM-1 | 5.12 (3.39-9.03) | 4.22 (3.05-6.02) | 0.026* |
| interleukin-2 | IL-2 | 14.91 (4.13-47.94) | 5.72 (2.46-20.14) | 0.005** |
| interleukin-8 | IL-8 | 8.84 (4.79-34.19) | 4.90 (3.00-12.28) | 0.002** |
| interleukin-12 subunit p70 | IL-12p70 | 18.97 (6.32-49.37) | 15.61 (7.59-38.33) | 0.73 |
| interleukin-1 beta | IL-1B | 5.90 (3.06-14.23) | 4.48 (2.77-10.07) | 0.14 |
| granulocyte-macrophage colony-stimulating factor | GM-CSF | 10.66 (3.64-38.94) | 8.20 (3.04-23.49) | 0.22 |
| interferon-gamma | IFN-γ | 15.45 (7.88-29.32) | 11.95 (4.65-23.70) | 0.032* |
| interleukin-6 | IL-6 | 13.80 (6.82-21.67) | 8.70 (3.88-18.46) | 0.010* |
| interleukin-10 | IL-10 | 18.84 (9.48-54.50) | 12.09 (6.96-19.29) | 0.0026** |
| tumor necrosis factor alpha | TNF-α | 28.52 (22.45-46.65) | 34.17 (23.26-53.74) | 0.57 |
| anti-*Saccharomyces cerevisiae* IgA | ASCAA | 19.33 (11.77-41.98) | 18.78 (11.41-47.65) | 0.83 |
| anti-*Saccharomyces cerevisiae* IgG | ASCAG | 10.91 (5.69-29.30) | 10.73 (3.88-33.21) | 0.40 |
| bacterial flagellin | CBir1 | 29.48 (21.30-42.72) | 30.81 (20.29-47.97) | 0.67 |
| bacterial flagellin | Fla2 | 23.42 (14.93-28.13) | 21.01 (15.79-29.11) | 0.48 |
| bacterial flagellin | FLAX | 33.56 (20.65-37.76) | 31.99 (24.62-40.26) | 0.47 |
| outer membrane porin C | OmpC | 9.76 (7.06-19.27) | 9.98 (6.50-15.62) | 0.38 |

Abbreviations: IQR, interquartile range; Ig, immunoglobulin
$^a$Statistical analysis performed with Mann-Whitney U test.
†p < 0.1;
*p < 0.05;
**p < 0.01;
***p < 0.001

Next, ROC analysis was performed for each marker individually. Several serum markers reached an area under the curve (AUC; with 95% confidence interval) higher than 0.60 with p<0.05. These markers were HGF (0.654; 0.574-0.733), TWEAK (0.619; 0.537-0.702), IFX trough levels (0.603; 0.520-0.685), CRP (0.647; 0.566-0.728), SAA (0.695; 0.618-0.773), IL-2 (0.621; 0.539-0.704), IL-8 (0.632; 0.550-0.714), IL-6 (0.611; 0.528-0.693) and 1-10 (0.630; 0.549-0.711). Further, in order to trace down co-linearity between the markers, non-parametric correlation analysis was performed. Four of the markers showed moderate co-linearity with correlation factors exceeding 0.7. These markers were VCAM-1 and ICAM-1 (r=0.735, p<0.0001) and GM-CSF and IL-2 (r=0.722, p<0.0001). A strong correlation was found between SAA and CRP (r=0.820, p<0.0001). Therefore, interaction terms were created and further explored with logistic regression analysis. Univariate binary logistic regression analysis was performed with internal validation through bootstrapping. As shown in Table 5, several serum markers were identified as markers associated with mucosal healing. Most significant associations (odds ratio; 95% confidence interval) with mucosal healing were found for the serum markers HGF (0.895; 0.812-0.956), TWEAK (1.032; 1.006-1.060), ICAM-1 (0.856; 0.739-0.950), VCAM-1 (0.933; 0.863-0.969) and OmpC (0.967; 0.934-1.000) (p<0.05). Interaction terms were also included in the analysis and ICAM-1 combined with VCAM-1 remained significant (0.991; 0.983-0.995).

TABLE 5

Binary univariate logistic regression analysis for serum markers.

| Univariate logistic regression | OR | 95% Confidence Interval | | Sig. (2-tailed) |
|---|---|---|---|---|
| | | Lower | Upper | |
| AREG | 0.996 | 0.979 | 1.069 | .293 |
| HBEGF | 0.990 | 0.945 | 1.104 | .334 |
| HGF | 0.895 | 0.812 | 0.956 | .003** |
| HRGB | 1.014 | 0.996 | 1.044 | .146 |
| BTC | 1.091 | 0.975 | 1.244 | .138 |
| EGF | 0.939 | 0.860 | 1.026 | .150 |
| TGFA | 0.961 | 0.779 | 1.337 | .300 |

TABLE 5-continued

Binary univariate logistic regression analysis for serum markers.

| Univariate logistic regression | OR | 95% Confidence Interval | | Sig. (2-tailed) |
|---|---|---|---|---|
| | | Lower | Upper | |
| FGF1 | 0.995 | 0.983 | 1.063 | .253 |
| FGF2 | 1.010 | 0.967 | 1.190 | .686 |
| FGF4 | 1.049 | 0.970 | 1.150 | .099* |
| FGF7 | 1.477 | 0.993 | 3.117 | .135 |
| FGF9 | 0.988 | 0.888 | 1.194 | .410 |
| SCF | 1.175 | 0.796 | 1.630 | .271 |
| TWEAK | 1.032 | 1.006 | 1.060 | .018** |
| IFX | 1.026 | 0.999 | 1.067 | .072* |
| ATI | 0.980 | 0.933 | 1.017 | .272 |
| CRP | 0.857 | 0.689 | 0.994 | .064* |
| CRP*SAA | 1.000 | 0.997 | 1.001 | .778 |
| SAA | 0.993 | 0.968 | 1.002 | .273 |
| ICAM-1 | 0.856 | 0.739 | 0.950 | .017** |
| ICAM-1*VCAM-1 | 0.991 | 0.983 | 0.995 | .007** |
| VCAM-1 | 0.933 | 0.863 | 0.969 | .007** |
| IL-2 | 0.999 | 0.994 | 1.001 | .586 |
| GM-CSF*IL-2 | 1.000 | 1.000 | 1.000 | .483 |
| IL-8 | 0.997 | 0.983 | 1.001 | .267 |
| IL-12p70 | 0.998 | 0.996 | 1.000 | .068* |
| IL-1B | 0.994 | 0.962 | 1.002 | .195 |
| GM-CSF | 0.999 | 0.992 | 1.002 | .286 |
| IFN-γ | 0.992 | 0.970 | 0.998 | .147 |
| IL-6 | 0.992 | 0.979 | 1.000 | .063* |
| IL-10 | 0.997 | 0.987 | 0.999 | .099* |
| TNFalpha | 0.999 | 0.990 | 1.001 | .743 |
| ASCAA | 1.002 | 0.990 | 1.015 | .674 |
| ASCAG | 0.995 | 0.973 | 1.017 | .657 |
| CBir1 | 1.005 | 0.985 | 1.026 | .579 |
| Fla2 | 1.015 | 0.980 | 1.051 | .365 |
| FLAX | 1.014 | 0.989 | 1.040 | .270 |
| OmpC | 0.967 | 0.934 | 1.000 | .033** | ii. Selection of the Best Subset of Markers Associated with Mucosal Healing with Multiple Logistic Regression Analysis.

As mentioned above, explorative univariate analysis defined more than 12 parameters that were associated with mucosal healing, however, for the selection of the best subset of markers through multiple logistic regression analysis we did not pre-select the variables based on their univariate properties. Multiple regression analysis using the Bayesian model averaging (BMA) method considered all serum parameters at start and retained 4 independent markers that were significantly associated with mucosal healing (HGF, BTC, TWEAK and VCAM-1) based on Bayesian information criterion (BIC) (Table 6 and FIG. 1). Fifty-six models were generated, of which the best 5 models are shown (cumulative posterior probability=0.3199). The final best model with a combination of 4 markers presented the highest posterior probability of 0.091. In this model HGF, BTC, TWEAK and VCAM-1 had a 76.2%, 31.3%, 23.9/% and 69.7% probability of being associated with mucosal healing, respectively. These results were internally validated with the use of bootstrapping.

TABLE 6

Multivariate logistic regression analysis using the BMA method.

| | p! = 0 | EV | SD | model 1 | model 2 | model 3 | model 4 | model 5 |
|---|---|---|---|---|---|---|---|---|
| Intercept | 100.0 | 0.78 | 0.99 | −0.37 | 0.23 | 1.72 | 1.69 | 2.23 |
| AREG | 0.0 | 0.00 | 0.00 | . | . | . | . | . |
| HBEGF | 0.0 | 0.00 | 0.00 | . | . | . | . | . |
| HGF | 76.2 | −0.09 | 0.07 | −0.14 | −0.14 | −0.09 | −0.09 | −0.10 |
| HRGB | 4.1 | 0.00 | 0.00 | . | . | . | . | . |
| BTC | 31.3 | 0.06 | 0.09 | 0.19 | 0.18 | . | . | . |
| EGF | 0.0 | 0.00 | 0.00 | . | . | . | . | . |
| TGFA | 0.0 | 0.00 | 0.00 | . | . | . | . | . |
| FGF1 | 0.0 | 0.00 | 0.00 | . | . | . | . | . |
| FGF2 | 0.0 | 0.00 | 0.00 | . | . | . | . | . |
| FGF4 | 0.7 | 0.00 | 0.00 | . | . | . | . | . |
| FGF7 | 10.3 | 0.06 | 0.20 | . | . | . | . | . |
| FGF9 | 0.0 | 0.00 | 0.00 | . | . | . | . | . |
| FGF19 | 0.5 | 0.00 | 0.01 | . | . | . | . | . |
| SCF | 0.0 | 0.00 | 0.00 | . | . | . | . | . |
| TWEAK | 23.9 | 0.01 | 0.02 | 0.03 | . | . | . | . |
| IFX | 9.3 | 0.00 | 0.01 | . | . | . | . | . |
| ATI | 0.0 | 0.00 | 0.00 | . | . | . | . | . |
| CRP | 0.0 | 0.00 | 0.00 | . | . | . | . | . |
| ICAM-1 | 12.9 | −0.02 | 0.06 | . | . | . | . | . |
| SAA | 0.0 | 0.0 | 0.00 | . | . | . | . | . |
| VCAM-1 | 69.7 | −0.05 | 0.04 | −0.07 | −0.07 | −0.08 | −0.07 | −0.07 |
| IL-2 | 0.0 | 0.00 | 0.00 | . | . | . | . | . |
| IL-8 | 0.0 | 0.00 | 0.00 | . | . | . | . | . |
| IL-12p70 | 29.3 | 0.00 | 0.00 | . | . | 0.00 | . | 0.00 |
| IL-1B | 0.0 | 0.00 | 0.00 | . | . | . | . | . |
| GM-CSF | 0.0 | 0.00 | 0.00 | . | . | . | . | . |
| IFNγ | 2.6 | 0.00 | 0.00 | . | . | . | . | . |
| IL-6 | 0.0 | 0.00 | 0.00 | . | . | . | . | . |
| IL-10 | 19.8 | 0.00 | 0.00 | . | . | . | 0.00 | . |
| TNF-α | 0.0 | 0.00 | 0.00 | . | . | . | . | . |
| ASCAA | 0.0 | 0.00 | 0.00 | . | . | . | . | . |
| ASCAG | 0.0 | 0.00 | 0.00 | . | . | . | . | . |
| CBir1 | 0.0 | 0.00 | 0.00 | . | . | . | . | . |
| Fla2 | 0.0 | 0.00 | 0.00 | . | . | . | . | . |
| FLAX | 0.0 | 0.00 | 0.00 | . | . | . | . | . |

TABLE 6-continued

Multivariate logistic regression analysis using the BMA method.

| | p! = 0 | EV | SD | model 1 | model 2 | model 3 | model 4 | model 5 |
|---|---|---|---|---|---|---|---|---|
| OmpC | 14.9 | −0.01 | 0.02 | . | . | . | . | −0.04 |
| nVar | | | | 4 | 3 | 3 | 3 | 4 |
| BIC | | | | −698.50 | −698.10 | −697.80 | −697.50 | −696.60 |
| post prob | | | | 0.09 | 0.08 | 0.07 | 0.06 | 0.04 |

Abbrevations:
p! = 0, Probability of the marker to be associated with mucosal healing;
EV, Posterior mean of the beta parameter;
SD, Standard deviation of each beta;
Model 1 . . . 5, Most probable multiple-marker models;
Post prob, Posterior probability of the model;
nVar, Number of markers included in the model;
BIC, Bayesian Information Criterion.

iii. Combined Biomarker Score for Assessment of Mucosal Healing.

Figure 2:
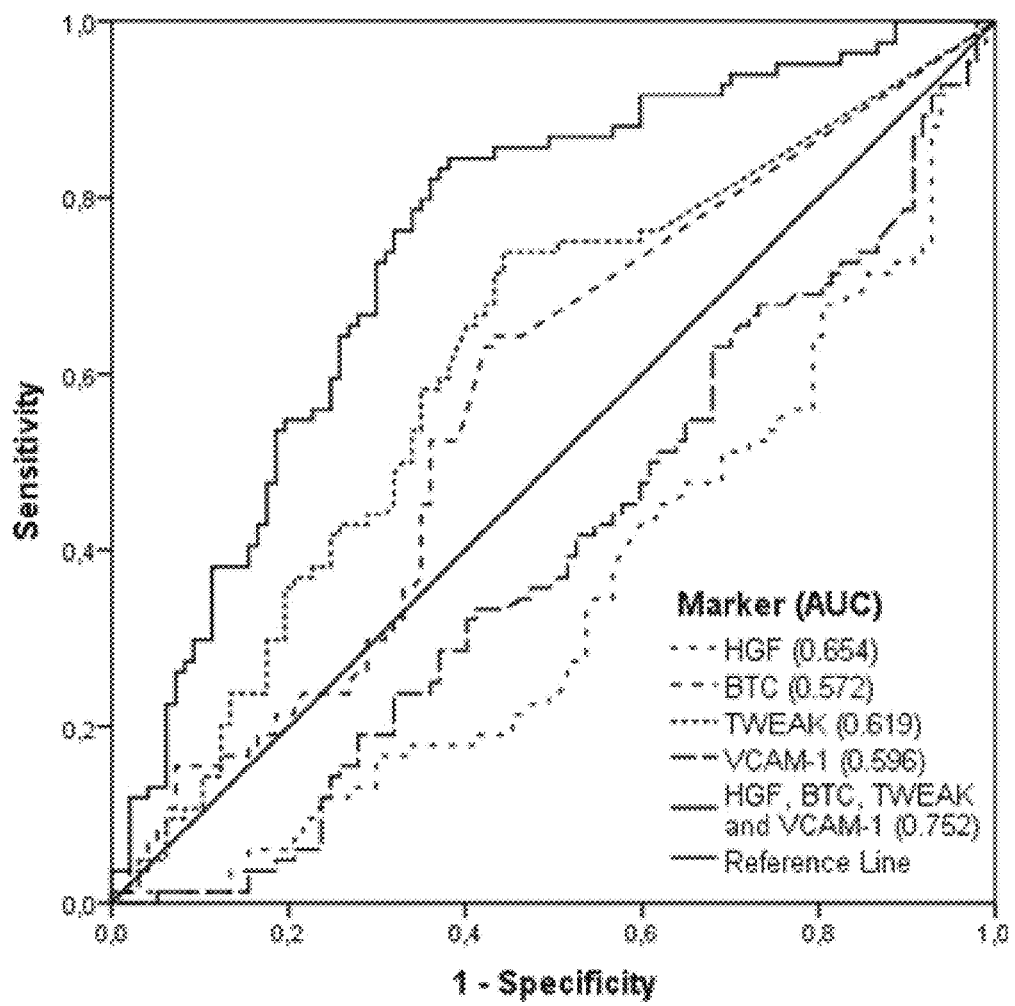
FIG. 2 illustrates a combined ROC curve of a 4-biomarker (e.g., HGF, BTC, TWEAK and VCAM-1) model and the individual markers. An AUC of 0.752 was found for the combination of biomarkers, whereas HGF, BTC, TWEAK or VCAM-1 alone had an AUC of 0.654, 0.572, 0.619, and 0.404, respectively.

Multiple logistic regression analysis provided the relative contribution of each individual marker in the final model and based on the regression equation a combined ROC curve was constructed. This combined ROC curve had an AUC of 0.75 (95% CI 0.68-0.82; p<0.0001) and was compared to the AUC of the individual marker ROC curves (HGF: 0.654, BTC: 0.572, TWEAK: 0.619 and VCAM-1: 0.596). As shown in FIG. 2, the combination of all 4 markers leads to a better association with mucosal healing than each of the markers alone.

Figure 3:
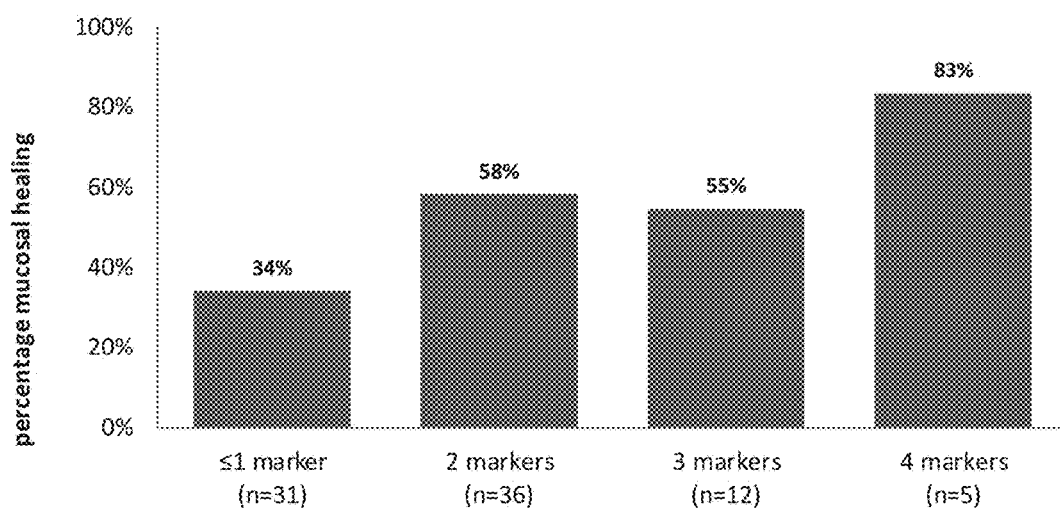
FIG. 3 illustrates a combined biomarker score for assessing mucosal healing. The combined biomarker score (ranging from 0 to 4) was generated by analyzing for each patient sample how many of the 4 biomarkers (e.g., HGF, BTC, TWEAK or VCAM-1) had levels above or below a specific cut-off value that was determined using ROC analysis.

Finally, a combined biomarker score (ranging from 0-4) was generated by analyzing for each sample how many of the 4 markers had levels above or below a certain cut-off point. The cut-off points were defined by individual ROC analysis and were determined as followed: HGF<11.42 CU/ml, BTC>11.44 CU/ml, TWEAK >20.62 CU/ml and VCAM-1<420 µg/ml. Cut-offs for BTC and TWEAK were above a certain marker level since these markers were positively associated with mucosal healing, whereas HGF and VCAM-1 were negatively associated with mucosal healing. The combined biomarker score resulted in a significant and gradual increased prediction of mucosal healing, whereby measuring all 4 markers lead to an 83% prediction of mucosal healing (FIG. 3, linear-by-linear p<0.001). The corresponding sensitivity and specificity percentages, positive predictive value (PPV) and negative predictive value (NPV) for the individual marker cut-off points and the biomarker score were also calculated. For HGF, BTC, TWEAK and VCAM-1, the sensitivity percentages were 69%, 32%, 45% and 61%, respectively; specificity percentages were 52%, 67%, 68% and 500/0, respectively; PPV were 59%, 46%, 55% and 58% respectively; and NPV were 62%, 53%, 59% and 53%, respectively. Measuring all 4 markers resulted in a sensitivity and specificity of 810% and 64%, with a PPV of 66% and a NPV of 80%.

Alternatively, the marker levels were divided into quartiles to evaluate the positive or negative dose response effect of BTC and TWEAK, and HGF and VCAM-1 on assessment of mucosal healing, respectively. The division of the 4 marker levels into quartiles is shown in FIG. 4A and each serum sample was assigned a score of 1 to 4 based on their designated quartile. As shown in FIG. 4B, a significant gradually increasing percentage of mucosal healing is found for decreasing levels of HGF (linear-by-linear, p=0.006) and VCAM-1 (linear-by-linear, p=0.042), with the highest percentages of healing associated to levels in quartile 1 (59% and 57%, respectively). In contrast, the percentage of mucosal healing was higher for increased levels of BTC (linear-by-linear, p=0.122) and TWEAK (linear-by-linear, p=0.006). For BTC, a higher percentage of healing was found in quartile 3 (65%) as compared to quartile 4 (44%). In the case of TWEAK, similar mucosal healing percentages were found for quartiles 1-2 (35% and 36%) and quartiles 3-4 (58%). The sum of scores was also calculated by inverting the quartile scores for BTC and TWEAK (levels in quartile 1 were given a score of 4, in quartile 2 a score of 3, etc.) to obtain a nice significant gradual increase of mucosal healing percentage for each decreasing quartile level with the highest percentage of mucosal healing (69%) associated to levels in quartile 1 (linear-by-linear, p<0.0001).

D. Discussion

In this study, serum levels of 36 different inflammatory, serologic or tissue repair markers as well as infliximab trough levels and antibodies to infliximab were measured in samples from CD patients under treatment with infliximab. Serum marker levels were correlated to mucosal healing status and evaluated for their association with healing. Through multiple regression analysis based on BIC, it was found that 4 serum markers (HGF, BTC, TWEAK and VCAM-1) were best associated with mucosal healing and combining the measurements of all 4 markers into a biomarker score increased the chance of an accurate assessment of mucosal healing to 83%. The biological relevance of measuring these markers was shown through quartile analysis, whereby HGF and VCAM-1 showed the best dose-response association with increasing percentages of mucosal healing with decreasing levels of both markers. Levels in quartile 1 for these markers were associated with 59%0 and 57% healing, respectively. BTC and TWEAK, however, showed an opposite trend, whereby increasing levels were associated with increasing percentage of mucosal healing. TWEAK hereby showed similar percentages of healing (58%) related to levels in quartiles 3 and 4, whereas quartile 3 levels (and not quartile 4 levels) for BTC were associated with the highest percentage of healing (65%). Measuring individual markers therefore seems plausible, however, when all 4 markers were measured simultaneously, the percentage of mucosal healing that was associated with marker levels in quartile 1 was increased to 69%. The positive cumulative effect of combining all 4 markers was also shown through ROC analysis, whereby a combined measurement lead to an AUC of 0.752 for prediction of healing with a sensitivity of 81%, specificity of 64%, a positive predictive value of 66% and negative predictive value of 80%.

To further underline the functional and biological relevance of these findings, previous studies that have investigated the 4 identified "healing markers" in IBD pathology were analyzed. Through microarray analysis it was determined that mRNA expression levels of HGF were upregulated in active CD patients, whereby CD patients responding to infliximab had significantly lower levels after treatment compared to CD non-responder patients. These data confirm the findings that lower HGF levels are found in patients who achieve mucosal healing as compared to patients that do not present mucosal healing. Another study by Matsuno et al. (*Res. Commun. Mol. Pathol. Pharmacol.*, 1997, 97:25-37) reported that HGF was elevated in patients with IBD and higher levels were found in patients with moderately severe to severe disease. Moreover, in an animal model of IBD, Thatch et al. (*J. Surg. Res.*, 2009, 156:245-249) described that HGF stimulates neovascularization while modulating the intestinal inflammatory response. In another study, Kanayama et al. (*Am. J. Physiol. Gastrointest. Liver. Physiol.*, 2007, 293:G230-239) investigated the effect of HGF on dextran sulfate sodium-induced colitis and found that HGF gene therapy was effective for the regeneration and repair of injured epithelial cells in inflammatory bowel disease. Whereas these animal models are studying the tissue repair effects of higher levels of HGF in acute inflammation, the patients presented herein are already in a state of mucosal healing, thereby higher levels of HGF are no longer needed. Therefore, low HGF levels are highly associated with mucosal healing in this study.

Not much is known about BTC in IBD. In a study by Chatterton et al. (*Int J Biochem Cell Biol.*, 2013, 45:1730-1747) looking at the anti-inflammatory mechanisms of bioactive milk proteins in the intestine of newborns, BTC was related to inflammation. Moreover in a study by Seno et al. it was shown that recombinant BTC had growth promoting activities equivalent to EGF, but was also found to exhibit a growth inhibitory effect on cells overexpressing EGF receptor (Seno et al., *Growth Factors*, 1996, 13:181-191). Based on our findings, it would therefore be interesting to investigate further the role of BTC in IBD and more specifically in tissue repair.

As a member of the TNF ligand family, TWEAK is able to activate fibroblast growth factor-inducible 14 (Fn14), a member of the TNF receptor family that is induced in a variety of cell types related to inflammation. In a review by Wajant et al. (*Br. J. Pharmacol.*, 2013, 136:912-923), it was reported that the TWEAK-Fn14 system results in the activation of the NFκB signaling pathway and plays a role in a number of pathologies. This was shown through several knock-out studies (experimental autoimmune encephalitis, rheumatoid arthritis and IBD). Moreover, a study by Dohi et al. (*Gastroenterology*, 2009, 136:912-923) investigating the effect of administering an anti-TWEAK monoclonal antibody in a TNBS mouse model of colitis, suggested that blocking TWEAK may dampen chronic intestinal inflammation and allow normal epithelial repair. However, the findings presented herein show that higher TWEAK levels were associated with healing. Since TWEAK is a multifunctional cytokine, similar in this regard to its sibling TNF, it has been proposed that TWEAK functions physiologically after acute injury and pathologically in chronic inflammatory disease settings (Burkly et al., *Am. J. Gastroenterol.*, 2011, 106:748-761). Thus, TWEAK might play a positive role in the disease, inducing the removal of dying cells and tissue debris, and promoting wound healing through controlled proliferation, migration of cells and extracellular matrix turnover. Its role in tissue repair might be specifically highlighted in the patient cohort of this study, since TNF is blocked in the CD patients by treatment with infliximab and TWEAK might therefore be more abundantly present or upregulated.

VCAM-1 is a cell adhesion molecule that helps regulate leukocyte adherence and infiltration towards inflammatory sites and is subsequently elevated in patients with IBD (Jones et al., *Gut*, 1995, 36:724-730). In a microarray study, it was found that VCAM-1 expression was significantly increased in inflamed colon of CD patients as compared to controls, and increased levels normalized after treatment with infliximab (Arijs et al., *Am. J. Gastroenterol.*, 2011, 106:748-761). Moreover, in a study by Soriano et al. (*Lab. Invest.*, 2000, 80:1541-1551), it was found that anti-VCAM1, but not anti-ICAM1 or anti-MAD-CAM 1 antibodies, ameliorated dextran sulfate sodium-induced colitis in mice. Furthermore, in a study by Jurisic et al. (*Genes Immun.*, 2010, 11:219-231), quantitative lymphatic vessel trait analysis in mice suggested that genetically determined expression differences of VCAM-1 were associated with susceptibility to colon inflammation, which was accompanied by extensive lymphatic vessel changes. VCAM-1 was therefore suggested as a promising therapeutic target for IBD.

In conclusion, provided herein is a panel of four surrogate serum markers which are associated with mucosal healing, whereby the combination of the four markers has the strongest association with healing. This panel can be used for the assessment of mucosal healing. It can also be used to follow up or monitor the effect of infliximab induction and maintenance therapies. In addition, this panel can be used to evaluate patients treated with other anti-TNF agents or newer anti-integrin therapies.

Example 2

Biomarker panel consisting of HGF, BTC, IFX trough levels and VCAM-1 for assessment of mucosal healing in patients with Crohn's Disease under infliximab therapy.

A. Methods

1. Patient Sampling

All participants were recruited between 1997 and 2009 via the University Hospital Leuven (Belgium). In this retrospective study, 181 serum samples were collected from 104 CD patients who started infliximab and who underwent serial endoscopies (before and during treatment with infliximab). The baseline characteristics of the CD patients are shown in Table 7.

TABLE 7

CD patient characteristics

| CD patient characteristics N = 104 | |
|---|---|
| male/female (%) | 51/53 (49/51) |
| median (IQR) age at sampling (years) | 43 (35-53) |
| median (IQR) age at diagnosis (years) | 21 (16-28) |
| location of disease at first infliximab (Vienna classification) (%) | |
| L1 | 13 (12) |
| L2 | 28 (27) |
| L3 | 58 (56) |
| L4 | 5 (5) |
| anal involvement (%) | 52 (50) |
| surgery prior to first colonoscopy (%) | 64 (62) |
| active smoking (%) | 35 (34) |
| concomitant medication (%) | |
| azathioprine (AZA) | 26 (25) |
| methotrexate (MTX) | 4 (4) |
| Steroids 11 | (11) |

Abbreviations: IQR, interquartile range

Forty-two patients gave one serum sample, 49 patients gave two serial serum samples and 13 patients gave 3 or more serial serum samples. The serum samples were available through the existing VLECC biobank and the study was approved by the University Hospital Ethics Committee. The majority of the patients had active inflammation with ulcers at start of treatment with infliximab, whereas only 4 patients had erosions with signs of active inflammation. Mucosal healing status was defined by an IBD-specialist at the time of endoscopy. Complete mucosal healing was defined as absence of ulcerations at follow-up endoscopy in patients who had ulcerations present at baseline ileocolonoscopy and partial mucosal healing was defined as clear endoscopic improvement, but with ulceration still present. In case of no endoscopic improvement or endoscopic worsening patients were classified as non-healers. A written informed consent was obtained from all individuals.

2. Serum Marker Level Measurements

All serum marker level measurements were performed at Prometheus Laboratories Inc. by experienced technicians blinded to the outcome parameters. Of the 181 collected serum samples, 50 samples were collected with a median (interquartile range, IQR) of 5 (0-29) days after the 1st scope, 59 samples with a median (IQR) of 0 (−11-7) days after the 2nd scope and 72 samples with a median (IQR) of 0 (−14-26) days after the 3rd scope. Collaborative Enzyme Enhanced Reactive (CEER) immunoassay, a proprietary highly sensitive protein micro-array developed by Prometheus Laboratories (San Diego, Calif.), was used for serum level measurements of amphiregulin (AREG), epiregulin (EREG) heparin-binding EGF-like growth factor (HBEGF), hepatocyte growth factor (HGF), heregulin beta EGF domain (HRGB), betacellulin (BTC), epidermal growth factor (EGF), transforming growth factor alpha (TGFA), fibroblast growth factor (FGF) 1, 2, 4, 7, 9 and 19, stem cell factor (SCF), tumor necrosis factor (TNF)-related weak inducer of apoptosis (TWEAK), platelet-derived growth factor beta (PDGFB) and vascular endothelial growth factor A (VEGFAX 16-18). Anti-*Saccharomyces cerevisiae* IgA (ASCAA), anti-*Saccharomyces cerevisiae* IgG (ASCAG), three bacterial flagellins (CBir1, Fla2 and FLAX) and outer membrane porin C (OmpC) were measured with the PROMETHEUS® IBD sgi Diagnostic™ test. Infliximab trough levels and antibodies to infliximab levels were measured by homogenous mobility shift assay (HMSA) as previously described(19). C-reactive protein (CRP), intercellular adhesion molecule-1 (ICAM-1), serum amyloid A (SAA), vascular cell adhesion molecule-1 (VCAM-1), interleukin (IL)-2, IL-6, IL-8, IL-10, IL-12p70 and IL-1β, granulocyte-macrophage colony-stimulating factor (GM-CSF), interferon-gamma (IFN-γ) and tumor necrosis factor alpha (TNF-α) were measured by ELISA.

All the serum markers and their functional properties are summarized in Table 8 and the detection limits of the tests per marker are listed in Table 9.

TABLE 8

| Functional group | Specific function | Marker name | Abbreviation |
| --- | --- | --- | --- |
| Growth and repair factors | member of the epidermal growth factor family | Amphiregulin | AREG |
| | member of the epidermal growth factor family | heparin-binding EGF-like growth factor | HBEGF |
| | cellular growth, motility and morphogenic factor - mucosal repair and fibrosis | hepatocyte growth factor | HGF |
| | member of the epidermal growth factor family | heregulin beta EGF domain | HRGB |
| | member of the epidermal growth factor family -mucosal repair | Betacellulin | BTC |
| | cell growth, proliferation, and differentiation | epidermal growth factor | EGF |
| | cell proliferation, differentiation and development | transforming growth factor alpha | TGFA |
| | modifier of endothelial cell migration and proliferation, angiogenic factor, fibrosis | fibroblast growth factor 1 | FGF1 |
| | wound healing, tumor growth, fibrosis | fibroblast growth factor 2 | FGF2 |
| | oncogenic growth factor, fibrosis | fibroblast growth factor 4 | FGF4 |
| | epithelial cell-specific growth factor, fibrosis | fibroblast growth factor 7 | FGF7 |
| | growth-stimulating effect, fibrosis | fibroblast growth factor 9 | FGF9 |
| | hormone produced in the ileum in response to bile acid absorption | fibroblast growth factor 19 | FGF19 |
| | stimulates stem cells to produce granulocytes (neutrophils, eosinophils, and basophils) and monocytes | granulocyte-macrophage colony-stimulating factor | GM-CSF |
| Hematopoiesis ligand | role in hematopoiesis, spermatogenesis and melanogenesis | stem cell factor | SCF |
| Pro-inflammatory markers | overlapping signaling functions with TNF, apoptosis, regulator of angiogenesis | tumor necrosis factor (TNF)-related weak inducer of apoptosis | TWEAK |
| | acute phase protein, binds to sugars and phosphocholine expressed on the surface of dead or dying cells (and some types of bacteria) to activate the complement system via the C1 complex | C-reactive protein | CRP |
| | transport of cholesterol to the liver for secretion into the bile, the recruitment of immune cells to inflammatory sites, and the induction of enzymes that degrade extracellular matrix | serum amyloid A | SAA |

TABLE 8-continued

| Functional group | Specific function | Marker name | Abbreviation |
|---|---|---|---|
| | endothelial- and leukocyte-associated transmembrane protein known for its importance in stabilizing cell-cell interactions and facilitating leukocyte endothelial transmigration | intercellular adhesion molecule-1 | ICAM-1 |
| | adhesion of lymphocytes, monocytes, eosinophils, and basophils to vascular endothelium | vascular cell adhesion molecule-1 | VCAM-1 |
| | growth, proliferation, and differentiation of T cells to 'effector' T cells | interleukin-2 | IL-2 |
| | mediator of fever and of the acute phase response | interleukin-6 | IL-6 |
| | induces chemotaxis and activation of primarily neutrophils | interleukin-8 | IL-8 |
| | differentiation of naive T cells into Th1 cells | interleukin-12 subunit p70 | IL-12p70 |
| | mediator of the inflammatory response, induces fever, acute phase response and cell proliferation, differentiation, and apoptosis. | interleukin-1 beta | IL-1β |
| | cytokine critical for innate and adaptive immunity against viral and intracellular bacterial infections and for tumor control | interferon-gamma | IFN-γ |
| | systemic inflammation, regulation of immune cells | tumor necrosis factor alpha | TNE-α |
| Anti-inflammatory marker | pleiotropic effects in immunoregulation and inflammation, downregulation of expression of Th1 cytokines, MHC class II antigens, and co-stimulatory molecules on macrophages, enhancement of B cell survival, proliferation, and antibody production | interleukin-10 | IL-10 |
| Serological markers | bacterial antibodies found in IBD patients, marker used for differential diagnosis of CD vs UC | anti-*Saccharomyces cerevisiae* IgA | ASCAA |
| | bacterial antibodies found in IBD patients, marker used for differential diagnosis of CD vs UC | anti-*Saccharomyces cerevisiae* IgG | ASCAG |
| | bacterial flagellin that represents systemic evidence of immune reactivity to specific components of the enteric microbiota | bacterial flagellin | CBir1 |
| | bacterial flagellin that represents systemic evidence of immune reactivity to specific components of the enteric microbiota | bacterial flagellin | Fla2 |
| | bacterial flagellin that represents systemic evidence of immune reactivity to specific components of the enteric microbiota | bacterial flagellin | FLAX |
| | major outer-membrane protein, originally isolated from *E. coli*, against which an excessive reactivity with antibodies has been reported in CD | outer membrane porin C | OmpC |
| Therapeutic markers | chimeric antibody levels directed towards TNF-α measured right before a new infusion of infliximab | Infliximab trough levels | IFX |
| | antibodies generated against infliximab that can cause loss of response | Antibodies to infliximab | ATI |

Detection limits (lower and upper) of all serum markers measured (Table 9) by Collaborative Enzyme Enhanced Reactive (CEER) immunoassay, ELISA, the IBD sgi Diagnostic test or Homogeneous Mobility Shift Assay (HMSA).

TABLE 9

|  | Marker | Detection limits | |
|---|---|---|---|
|  |  | Lower | Upper |
| CEER (CU/ml) | AREG | 1.25 | 10 |
|  | EREG | 50 | 400 |
|  | HBEGF | 1.25 | 10 |
|  | HGF | 4 | 32 |
|  | HRG | 6 | 48 |
|  | BTC | 8 | 64 |
|  | EGF | 0.624 | 40 |
|  | TGFA | 0.6 | 4.8 |
|  | FGF1 | 6 | 48 |
|  | FGF2 | 3 | 24 |
|  | FGF4 | 5 | 40 |
|  | FGF7 | 0.95 | 7.6 |
|  | FGF9 | 3 | 24 |
|  | FGF19 | 12.5 | 100 |
|  | SCF | 1.25 | 10 |
|  | TWEAK | 2.5 | 20 |
|  | PDGFB | 15 | 120 |
|  | VEGFA | 2.5 | 20 |
| ELISA (µg/ml) | CRP | 3.1 | 200 |
|  | ICAM-1 | 3.1 | 200 |
|  | SAA | 3.1 | 200 |
|  | VCAM-1 | 3.1 | 200 |
|  | IL-2 | 3.1 | 200 |
|  | IL-8 | 3.1 | 200 |
|  | IL-12p70 | 3.1 | 200 |
|  | IL-1β | 3.1 | 200 |
|  | GM-CSF | 3.1 | 200 |
|  | IFN-γ | 3.1 | 200 |
|  | IL-6 | 3.1 | 200 |
|  | IL-10 | 3.1 | 200 |
|  | TNF-α | 3.1 | 200 |
| IBD sgi diagnostic test (µg/ml) | ASCAA | 3.1 | 200 |
|  | ASCAG | 3.1 | 200 |
|  | CBir1 | 3.1 | 200 |
|  | Fla2 | 3.1 | 200 |
|  | FLAX | 3.1 | 200 |
|  | OmpC | 3.1 | 200 |
| HMSA (µg/ml) | IFX trough | 0.98 | 34 |
|  | ATI | 0.98 | 34 |

As shown in Table 10, several serum markers were significantly associated with mucosal healing (p<0.05) using Binary univariate logistic regression analysis. Significant associations (odds ratio (OR); 95% CI) were found for HGF (0.92; 0.84-0.98), BTC (1.17; 1.06-1.33), TWEAK (1.03; 1.00-1.05), IFX trough levels (1.03; 1.00-1.07), CRP (0.98; 0.95-1), ICAM-1 (0.87; 0.74-0.96) and VCAM-1 (0.93; 0.84-0.98). After exclusion of the samples matched to partial healing at endoscopic evaluation (n=19), 11 markers (HGF, BTC, TWEAK, IFX trough levels, CRP, ICAM-1, SAA, VCAM-1, IL-2, IL-10 and OmpC) had significantly different levels in samples matched to no healing as compared to samples matched to complete mucosal healing (Mann-Whitney U test p<0.05).

TABLE 10

| Univariate logistic regression | OR | 95% CI | | p-value$_a$ |
|---|---|---|---|---|
|  |  | Lower | Upper |  |
| AREG (CU/ml) | 1.00 | 0.96 | 1.05 | 0.344 |
| HBEGF (CU/ml) | 0.99 | 0.94 | 1.13 | 0.402 |
| HGF (CU/ml) | 0.92 | 0.84 | 0.98 | 0.027* |
| HRGB (CU/ml) | 1.02 | 1.00 | 1.05 | 0.092 |
| BTC (CU/ml) | 1.17 | 1.06 | 1.33 | 0.004** |
| EGF (CU/ml) | 0.93 | 0.83 | 1.02 | 0.104 |
| TGFA (CU/ml) | 0.97 | 0.73 | 1.29 | 0.364 |
| FGF1 (CU/ml) | 1.00 | 0.99 | 1.08 | 0.481 |
| FGF2 (CU/ml) | 1.02 | 0.98 | 1.22 | 0.509 |
| FGF4 (CU/ml) | 1.02 | 0.94 | 1.11 | 0.409 |
| FGF7 (CU/ml) | 1.13 | 0.83 | 3.09 | 0.462 |
| FGF9 (CU/ml) | 0.99 | 0.94 | 1.25 | 0.313 |
| FGF19 (CU/ml) | 1.06 | 0.01 | 1.21 | 0.223 |
| SCF (CU/ml) | 1.17 | 0.8 | 1.71 | 0.293 |
| TWEAK (CU/ml) | 1.03 | 1.00 | 1.05 | 0.039* |
| IFX (µg/ml) | 1.03 | 1.00 | 1.07 | 0.017* |
| ATI (µg/ml) | 0.99 | 0.93 | 1.02 | 0.456 |
| CRP (mg/L) | 0.98 | 0.95 | 1.00 | 0.048* |
| ICAM (0.1 mg/L) | 0.87 | 0.74 | 0.96 | 0.029* |
| SAA (mg/L) | 0.99 | 0.96 | 1.00 | 0.377 |
| VCAM-1 (0.1 mg/L) | 0.93 | 0.84 | 0.98 | 0.03* |
| IL-2 (µg/ml) | 1.00 | 0.99 | 1.00 | 0.154 |
| IL-8 (10 µg/ml) | 1.00 | 0.98 | 1.00 | 0.374 |
| IL-12p70 (µg/ml) | 1.00 | 1.00 | 1.00 | 0.164 |
| IL-1β (µg/ml) | 0.99 | 0.95 | 1.00 | 0.308 |
| GM-CSF (µg/ml) | 1.00 | 0.99 | 1.00 | 0.294 |
| IFN-γ (µg/ml) | 0.99 | 0.97 | 1.00 | 0.228 |
| IL-6 (µg/ml) | 0.99 | 0.98 | 1.00 | 0.176 |
| IL-10 (µg/ml) | 1.00 | 0.99 | 1.00 | 0.123 |
| TNFalpha (µg/ml) | 1.00 | 0.99 | 1.00 | 0.948 |
| ASCAA (µg/ml) | 1.00 | 0.98 | 1.01 | 0.602 |
| ASCAG (µg/ml) | 1.00 | 0.97 | 1.02 | 0.839 |
| CBir1 (µg/ml) | 1.00 | 0.98 | 1.02 | 0.845 |
| Fla2 (µg/ml) | 1.02 | 0.98 | 1.06 | 0.232 |
| FLAX (µg/ml) | 1.01 | 0.99 | 1.04 | 0.293 |
| OmpC (µg/ml) | 0.97 | 0.94 | 1.01 | 0.119 |

Abbreviations: OR, odds ratio; CI, confidence interval
$_a$Statistical analysis performed with binary logistic regression in SPSS.
*p < 0.05;
**p < 0.01

Table 11 shows serum marker characteristics after exclusion of partial healing samples. Serum marker levels matched to complete versus no mucosal healing were compared with the use of the Mann-Whitney U test. The AUC indicates the performance of these markers to discriminate mucosal healing. Univariate logistic regression analysis was performed to investigate the association with mucosal healing. The odds ratios represent a negative (<1) or positive (>1) association with healing.

TABLE 11

| Marker | Median (IQR) complete healing (n = 48) | Median (IQR) no healing (n = 114) | p-value | AUC (95% CI) | OR | p-value |
|---|---|---|---|---|---|---|
| HGF | 11.06 (9.19-13.14) | 12.56 (10.05-16.15) | 0.017** | 0.619 (0.526-0.711) | 0.922 | 0.039* |
| BTC | 10.56 (8-12.37) | 8 (811.89) | 0.017* | 0.611 (0.518-0.705) | 1.146 | 0.031* |

TABLE 11-continued

| Marker | Median (IQR) complete healing (n = 48) | Median (IQR) no healing (n = 114) | p-value | AUC (95% CI) | OR | p-value |
|---|---|---|---|---|---|---|
| TWEAK | 19.98 (16.25-26.39) | 15.18 (2.5-23.84) | 0.015* | 0.619 (0.528-0.710) | 1.031 | 0.031* |
| IFX | 4.25 (0.98-12.42) | 1.46 (0.98-8.06) | 0.04* | 0.600 (0.505-0.694) | 1.03 | 0.074 |
| CRP | 3.8 (0.85-10) | 9 (2.8-30.2) | 0.001*** | 0.669 (0.576-0.762) | 0.981 | 0.043* |
| ICAM-1 | 2.5 (1.90-3.49) | 3.12 (2.24-4.45) | 0.007** | 0.635 (0.544-0.726) | 0.801 | 0.021* |
| SAA | 1.65 (0.87-6.89) | 6.79 (2.53-24.29) | <0.001*** | 0.704 (0.609-0.798) | 0.996 | 0.455 |
| VCAM-1 | 3.92 (2.92-5.4) | 5.13 (3.54-8.53) | 0.003** | 0.647 (0.557-0.738) | 0.917 | 0.036* |
| IL-2 | 5.3 (1.97-22.75) | 13.34 (3.57-45.46) | 0.037* | 0.604 (0.505-0.703) | 0.999 | 0.333 |
| IL-10 | 11.74 (6.44-21.47) | 18.00 (8.48-42.72) | 0.022* | 0.614 (0.519-0.710) | 0.997 | 0.233 |
| OmpC | 8.89 (6.27-12.45) | 10.08 (7.01-18.19) | 0.044* | 0.600 (0.511-0.690) | 0.939 | 0.014* |

Abbreviations:
IQR, interquartile range;
AUC, area under the curve;
CI, confidence interval;
OR, odds ratio.
*p <0.05,
**p <0.01,
***p <0.001

3. Missing Values and Outliers

Markers that had more than 20 percent missing values due to sample limit or technical problems were excluded from further analyses (this was the case for PDGFB, VEGFA and EREG). FGF2 and FGF7 had 10.8 and 12.9 percent of missing values, respectively, but were not excluded from further analyses. In the remaining dataset, missing values (min. n=5, max. n=24) were replaced with the median of the series per marker with the use of simple imputation in SPSS. To detect influential observations in our dataset, we looked at Cook's distance values that exceeded 1 after binary logistic regression analysis. This resulted in the exclusion of 5 serum samples (belonging to 5 CD patients) that were identified as outliers influencing the final results due to extreme values.

4. Statistical Analysis

Several univariate analyses were performed to investigate the individual association of each marker with mucosal healing. These analyses included Mann-Whitney U test, Receiver operating characteristic (ROC) analyses and binary logistic regression. Multiple logistic regression analysis was performed with the Bayesian model averaging (BMA) package in R to select the best subset of markers associated with mucosal healing. Selection of the final model was based on Bayesian information criterion (BIC). In a separate analysis, samples matched to partial mucosal healing were excluded. This was done to investigate true mucosal healing markers without bias of partial healing. Statistical analyses were performed in SPSS (version 22) and R (version 3.0.2) and p-values <0.05 were considered significant.

A. Results

Figure 8:
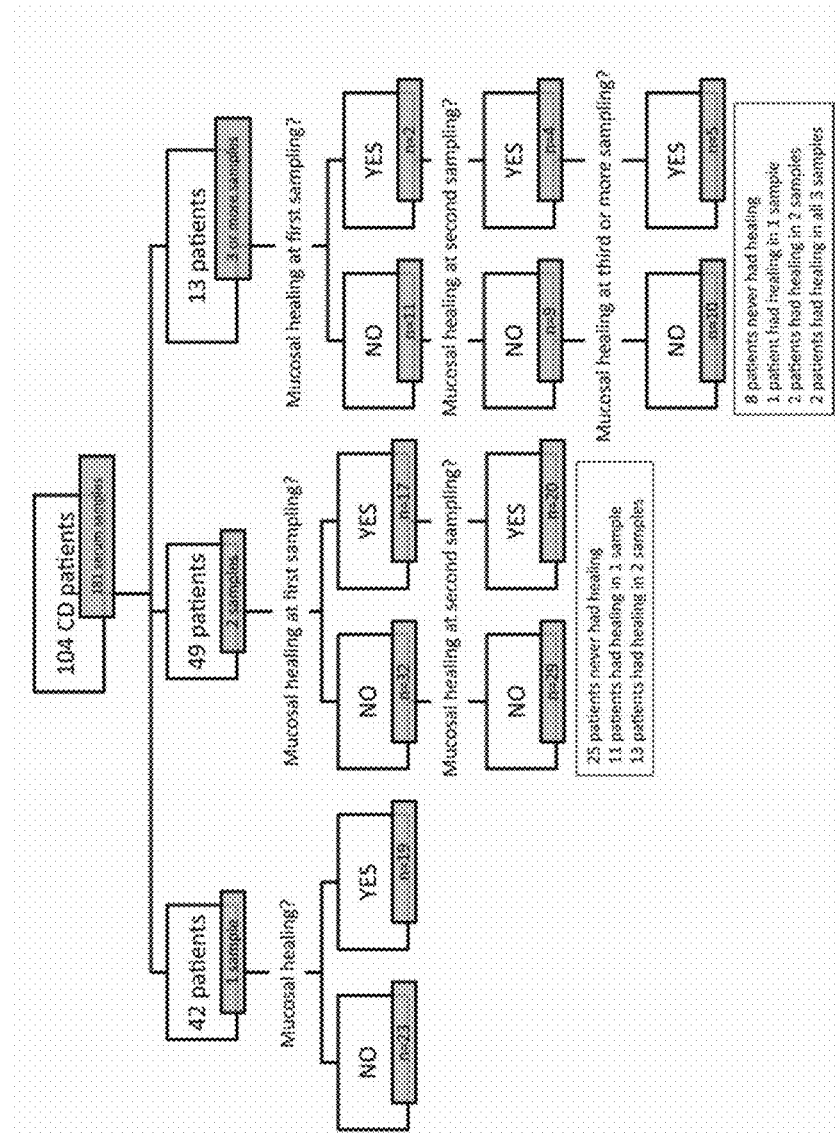
FIG. 8 illustrates a flow chart of the distribution of serum samples per patient and the amount of samples that were matched to healing. As shown therein, of the 181 serum samples, 114 samples were matched to no mucosal healing at endoscopic evaluation, whereas 67 samples were matched to complete (n=48) or partial (n=19) mucosal healing. Comparison of marker levels between samples matched to no healing versus samples matched to mucosal healing at endoscopic evaluation identified 14 markers (HGF, BTC, FGF1, FGF2, TWEAK, IFX trough levels, CRP, ICAM-1, SAA, VCAM-1, IL-2, IL-8, IL-6 and IL-10) of which the levels were significantly different between both groups (Mann-Whitney U test, p<0.05).

1. Univariate Analyses Identified Several Markers Associated with Mucosal Healing A flow chart of the distribution of serum samples per patient and the amount of samples that were matched to healing is given in FIG. 8. Of the 181 serum samples, 114 samples were matched to no mucosal healing at endoscopic evaluation, whereas 67 samples were matched to complete (n=48) or partial (n=19) mucosal healing. Comparison of marker levels between samples matched to no healing versus samples matched to mucosal healing at endoscopic evaluation identified 14 markers (HGF, BTC, FGF1, FGF2, TWEAK, IFX trough levels, CRP, ICAM-1, SAA, VCAM-1, IL-2, IL-8, IL-6 and IL-10) of which the levels were significantly different between both groups (Mann-Whitney U test, p<0.05) (Table 12).

Serum marker characteristics. Serum marker levels matched to mucosal healing versus no mucosal healing were compared with the use of the Mann-Whitney U test. The area under the curve (AUC) indicates the performance of these markers to assess mucosal healing.

TABLE 12

| Marker | Median (IQR) ho healing (n = 114) | Median (IQR) mucosal healing (n = 67) | p-value$^a$ | AUC (95% CI) |
|---|---|---|---|---|
| AREG (CU/ml) | 1.97 (1.25-6.61) | 1.98 (1.25-6.72) | 0.67 | 0.518 (0.431-0.606) |
| HBEGF (CU/ml) | 4.24 (3.52-5.93) | 4.26 (3.54-6.38) | 0.70 | 0.517 (0.43-0.605) |
| HGF (CU/ml) | 12.56 (10.05-16.15) | 11.37 (9.62-12.69) | 0.01* | *0.616 (0.533-0.698) |
| HRGB (CU/ml) | 6 (6-10.12) | 6 (6-19.87) 7 | 0.33 | 0.537 (0.44-0.627) |
| BTC (CU/ml) | 8 (8-11.89) | 10.84 (8-12.23) | 0.003** | 0.626 (0.543-0.709) |
| EGF (CU/ml) | 5.05 (3.1-8.52) | 4.48 (2.66-7.17) | 0.19 | 0.558 (0.473-0.644) |
| TGFA (CU/ml) | 1.1 (0.93-1.48) | 1.1 (0.9-1.49) | 0.81 | 0.511 (0.423-0.599) |

TABLE 12-continued

| Marker | Median (IQR) ho healing (n = 114) | Median (IQR) mucosal healing (n = 67) | p-value[a] | AUC (95% CI) |
|---|---|---|---|---|
| FGF1 (CU/ml) | 9.79 (6-12.31) | 10.57 (8.58-15.15) | 0.03* | 0.599 (0.513-0.684) |
| FGF2 (CU/ml) | 3 (3-3) | 3 (3-5.35) | 0.03* | 0.575 (0.487-0.663) |
| FGF4 (CU/ml) | 6.98 (5-9.52) | 7.15 (5-10.35) | 0.61 | 0.522 (0.433-0.611) |
| FGF7 (CU/ml) | 1.33 (0.95-1.61) | 1.33 (0.95-1.74) | 0.16 | 0.561 (0.474-0.649) |
| FGF9 (CU/ml) | 3 (3-4.68) | 3.9 (3-5.12) | 0.19 | 0.553 (0.466-0.641) |
| FGF19 (CU/ml) | 12.5 (12.5-12.5) | 12.5 (12.5-12.5) | 0.86 | 0.503 (0.416-0.59) |
| SCF (CU/ml) | 1.43 (1.25-2.41) | 1.78 (1.25-2.33) | 0.32 | 0.542 (0.455-0.629) |
| TWEAK (CU/ml) | 15.18 (2.5-23.84) | 19.68 (15.95-26.08) | 0.02* | 0.600 (0.516-0.684) |
| IFX (µg/ml) | 1.46 (0.98-8.06) | 3.88 (0.98-12.88) | 0.04* | 0.588 (0.502-0.675) |
| ATI (µg/ml) | 0.98 (0.98-0.98) | 0.98 (0.98-0.98) | 0.77 | 0.508 (0.421-0.595) |
| CRP (mg/L) | 0.9 (0.28-3.02) | 0.29 (0.09-1) | <0.001*** | 0.669 (0.586-0.751) |
| ICAM-1 (0.1 mg/L) | 3.12 (2.24-4.45) | 2.57 (1.96-3.65) | 0.02* | 0.604 (0.519-0.688) |
| SAA (mg/L) | 6.79 (2.53-24.29) | 1.8 (0.87-6.87) | <0.001*** | 0.695 (0.613-0.777) |
| VCAM-1 (0.1 mg/L) | 5.13 (3.54-8.53) | 4.1 (3-5.9) | 0.01** | 0.610 (0.526-0.693) |
| IL-2-(µg/ml) | 13.34 (3.57-45.46) | 5.69 (2.09-19.72) | 0.01** | 0.615 (0.53-0.701) |
| IL-8 (10 µg/ml) | 8.22 (3.77-27.45) | 5.24 (3.55-12.18) | 0.04* | 0.590 (0.506-0.674) |
| IL-12p70 (µg/ml) | 20.28 (6.96-50.8) | 15.22 (6.19-37.54) | 0.37 | 0.540 (0.455-0.625) |
| IL-1β (µg/ml) | 5.20 (2.95-13.99) | 4.75 (2.92-9.98) | 0.20 | 0.557 (0.472-0.642) |
| GM-CSF (µg/ml) | 10.43 (3.81-33.98) | 6.34 (2.38-22.97) | 0.06 | 0.585 (0.498-0.671) |
| IFNγ (µg/ml) | 14.72 (7.75-28.7) | 12.65 (4.24-20.98) | 0.05 | 0.588 (0.502-0.674) |
| IL-6 (µg/ml) | 12.85 (6.17-19.86) | 8.83 (3.34-18.48) | 0.03* | 0.595 (0.507-0.683) |
| IL-10 (µg/ml) | 18.00 (8.48-42.72) | 11.75 (7-19.24) | 0.01* | 0.620 (0.536-0.704) |
| TNF-α (µg/ml) | 29.5 (22.67-53.06) | 31.85 (20.78-48.53) | 0.72 | 0.516 (0.428-0.604) |
| ASCAA (µg/ml) | 19.91 (11.84-46.59) | 18.34 (11.3-43.63) | 0.69 0.518 | (0.431-0.604) |
| ASCAG (µg/ml) | 11.02 (5.39-28.63) | 10.65 (3.86-33.27) | 0.51 | 0.529 (0.439-0.619) |
| CBir1 (µg/ml) | 29.93 (20.63-44.35) | 30.44 (20.65-47.39) | 0.95 | 0.503 (0.415-0.591) |
| Fla2 (µg/ml) | 22.73 (14.86-28.11) | 20.98 (16.52-29.15) | 0.33 0.546 | (0.459-0.633) |
| FLAX (µg/ml) | 33.09 (20.64-37.8) | 31.97 (25.04-40.26) | 0.32 | 0.456 (0.37-0.542) |
| OmpC (µg/ml) | 10.08 (7.01-18.19) | 9.45 (6.4-14.67) | 0.25 | 0.551 (0.466-0.636) |

Abbreviations: IQR, interquartile range; CI, confidence interval
[a]Statistical analysis performed with Mann-Whitney U test in SPSS.
*p < 0.05;
**p < 0.01;
***p < 0.001

For most of these markers, lower levels were found in samples matched to mucosal healing. However, for BTC, FGF1, FGF2, TWEAK and IFX trough levels, higher levels were found in samples matched to mucosal healing. The discriminative performance of these markers was further investigated with the use of ROC analysis. The area under the curve (AUC) values and the corresponding 95% confidence interval (CI) are listed in Table 12.

2. Selection of the Best Subset of Markers Associated with Mucosal Healing by Multiple Logistic Regression Analysis Multiple logistic regression analysis included all 36 markers and the best model was chosen based on BIC. The final model contained 4 markers (HGF, BTC, IFX trough levels and VCAM-1) that were significantly associated with mucosal healing (Table 13).

TABLE 13

Multivariate logistic regression analysis. Selection of the best subset of markers associated with mucosal healing based on BIC.

| Marker | β coefficient | OR (95% CI) | p-value |
|---|---|---|---|
| HGF | −0.14 | 0.87 (0.77-0.93) | 0.002 |
| BTC | 0.27 | 1.31 (1.14-1.59) | <0.001 |
| IFX trough | 0.04 | 1.04 (1.00-1.08) | 0.02 |
| VCAM-1 | −0.08 | 0.93 (0.80-0.98) | 0.03 |
| BIC | −710.14 | | |

Abbrevations: BIC, Bayesian Information Criterion; OR, odds ratio; CI, confidence interval.

Figure 5:
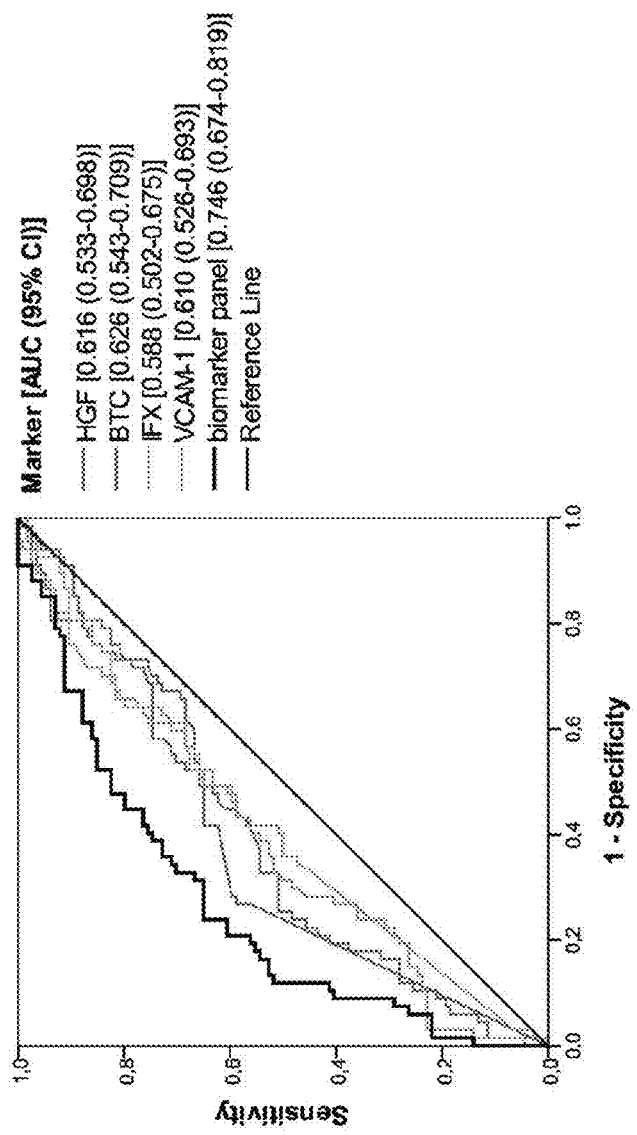
FIG. 5 illustrates combined ROC curves for an embodiment of 4 selected markers individually and the combined biomarker panel for association with (complete and partial) mucosal healing. The area under the curve (AUC) and the 95% confidence interval (CI) are shown.

The following regression equation was obtained: P(y=1)=−1.36+(−0.14*HGF)+(0.27*BTC)+(0.04*IFX trough)+(−0.08*VCAM-1). The predicted probability values generated by the multiple regression equation were investigated by ROC analysis and generated an AUC (CI 95%) of 0.746 (0.674-0.819) (FIG. 5). Compared to the individual AUC's of HGF [0.616 (0.533-0.698)], BTC [0.626 (0.543-0.709)], IFX trough levels [0.588 (0.502-0.675)] and VCAM-1 [0.610 (0.526-0.693)], the combination of all 4 markers had a higher performance to discriminate mucosal healing than the best individual marker BTC (likelihood ratio test: $\chi^2$=52.8, df=3, p<0.001). After exclusion of the serum samples matched to partial healing, 3 predictors were retained after multiple regression analysis. The 3 predictors and their corresponding OR (95% CI) were HGF [0.89 (0.75-0.97)], BTC [1.26 (1.12-1.51)] and VCAM-1 [0.91 (0.73-0.98)]. The predicted probability values generated by the multiple regression equation were investigated by ROC analysis and generated an AUC (CI 95%) of 0.737 (0.654-0.820).

5. Biomarker Score for Assessment of Mucosal Healing.

Figure 6:
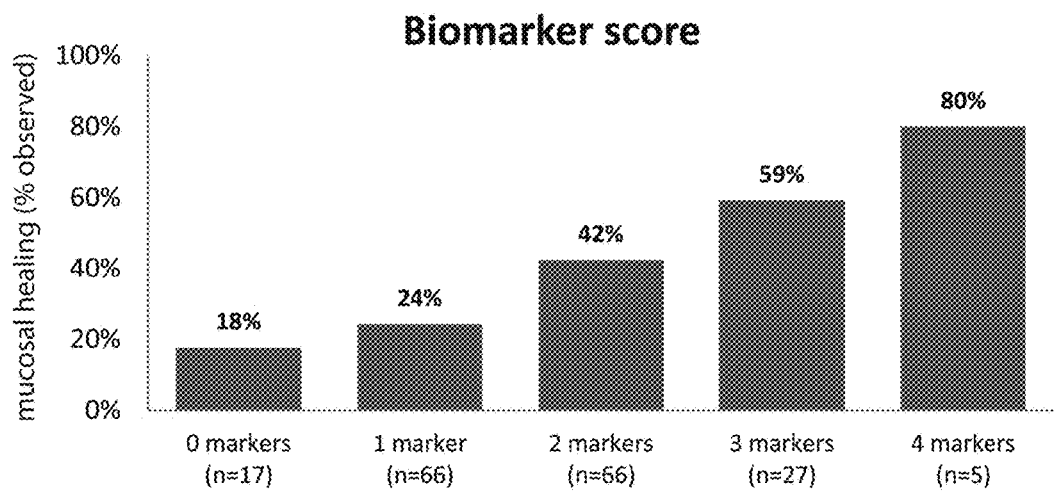
FIG. 6 illustrates a biomarker score for assessment of mucosal healing. The biomarker score (ranging from 0-4) was generated by analyzing for each sample how many of the 4 markers (e.g., HGF, BTC, IFX trough levels or VCAM-1) had amounts or levels above or below a certain cut-off point that was determined by ROC analysis. A positive test result for all 4 markers was observed in 80% of the samples matched to mucosal healing (linear trend test, p<0.001).

Finally, a biomarker score (ranging from 0-4) was generated by analyzing for each serum sample how many of the 4 markers had levels above or below a certain cut-off point. The cut-off points were defined by individual ROC analysis based on the combination of high sensitivity and specificity percentages. HGF levels <11.42 CU/ml, BTC levels >10.3 CU/ml, IFX trough levels >5.8 µg/ml and VCAM-1 levels <420 µg/ml were associated with a higher probability of mucosal healing. The biomarker score resulted in a significant and gradual increased observation of mucosal healing, whereby a positive test result of all 4 markers was observed in 80% of the samples matched to mucosal healing (FIG. 6, linear trend test p<0.001).

To investigate the performance of this biomarker score to discriminate mucosal healing, ROC analysis defined an AUC (95% CI) of 0.673 (0.592-0.755). Similar analyses were performed after exclusion of the serum samples matched to partial healing and we found that a biomarker score of 3, with a positive test result for all 3 markers, was observed in 64% of the samples matched to mucosal healing. The AUC (95% CI) of the biomarker score was 0.676 (0.586-0.766). Alternatively, the marker levels were divided into quartiles to evaluate the dose response effect of these markers on the assessment of mucosal healing. The division of the 4 marker levels into quartiles is shown in FIG. 7A and each serum sample was assigned a score of 1 to 4 based on their designated quartile. The quartile scores were given according to the positive or negative association with healing. Therefore, lower levels of HGF and VCAM-1 were given a score of 4, whereas lower levels of BTC and IFX trough were given a score of 1. As shown in FIG. 7B, a significant gradually increasing probability of mucosal healing was found for decreasing levels of HGF (linear trend test, p=0.036) and VCAM-1 (linear trend test, p=0.029), with the highest probabilities of healing associated to levels in quartiles 2 and 1 (42% and 50%), respectively. In contrast, the probability of mucosal healing was higher for increased levels of BTC (linear trend test, p=0.007) and IFX trough (linear trend test, p=0.035). For BTC, a higher probability of healing was found in quartiles 2 and 3 (59% and 57%) as compared to quartile 4 (40%). In the case of IFX trough levels, a gradually increasing mucosal healing probability was found with the highest probability for levels in quartile 4 (51%). The sum of all quartile scores was then calculated (FIG. 7C) and divided into quartiles again. A positive test result for all 4 markers (score 4) was observed in 67% of the samples matched to mucosal healing (linear trend test, p<0.001) (FIG. 7B). ROC determined an AUC of 0.702 (0.623-0.781) for using the quartile of the sum of quartile scores. Finally, these results were compared to quartile analysis performed on samples matched to complete or no healing, with exclusion of the partial healing samples. A positive test result for all 3 markers was observed in 59% of the samples matched to mucosal healing. The AUC (95% CI) for this combined quartile score was 0.714 (0.629-0.800).

Discussion

The markers studied in this cohort included several growth and repair factors, including 5 members of the epidermal growth factor family (AREG, HBEGF, HRGB, BTC and EGF), HGF, TGFA, GM-CSF and 6 members of the FGF family. A range of pro-inflammatory markers was also studied, including several interleukins [IL-1β, IL-2, IL-6, IL-8 and IL-12p70], acute phase proteins (CRP and SAA), cell adhesion molecules (VCAM-1 and ICAM-1), TWEAK, IFN-γ and TNF-α. IL-10 as anti-inflammatory marker was also investigated. Furthermore, a serology panel consisting of six bacterial markers was measured. The panel included ASCAA and ASCAG, as well as antibodies against three bacterial flagellins (CBir1, Fla2 and FLAX) and OmpC. Finally, SCF was also included in the analysis.

Multiple logistic regression analysis retained 4 serum markers (HGF, BTC, IFX trough and VCAM-1) in the final model based on BIC. The cumulative effect of combining all 4 markers was shown through ROC analysis, whereby a combined measurement lead to an AUC of 0.746 for discrimination of mucosal healing with a sensitivity of 79% and specificity of 61%. In addition, a biomarker score was generated based on the individual marker cut-offs as determined by ROC analysis and a positive test result for all 4 markers was observed in 80% of the samples matched to mucosal healing (AUC of 0.673). The biological relevance of measuring these markers was further shown through quartile analysis, whereby VCAM-1 and HGF showed a clear dose-response effect with increasing probabilities of mucosal healing for decreasing levels of both markers. BTC and IFX trough showed an opposite trend, whereby increasing levels were associated with increasing probability of mucosal healing. For BTC, however, the highest probability of mucosal healing was found for levels in quartiles 2 and 3, and not in quartile 4. In clinical practice, the measurement of individual markers therefore seems plausible; however, when the measurements of all 4 markers were combined, the observation of mucosal healing for combined levels in quartile 4 was 67% (AUC of 0.702).

To further underline the functional and biological relevance of these findings, we looked at previous studies in which the 4 identified "healing markers" were investigated in IBD pathology. HGF is one of several growth factors (including EGF and VEGF) that have been demonstrated to enhance epithelial cell restitution through a TGF-β dependent pathway (see, Sturm A, Dignass A U. Epithelial restitution and wound healing in inflammatory bowel disease. World J Gastroenterol 2008; 14:348-53, Goke M, Kanai M, Podolsky D K. Intestinal fibroblasts regulate intestinal epithelial cell proliferation via hepatocyte growth factor. Am J Physiol 1998; 274:G809-18). Matsuno and colleagues reported that HGF was elevated in patients with IBD and higher levels were found in patients with moderately severe to severe disease (see, Matsuno M, Shiota G, Umeki K, et al. Clinical evaluation of hepatocyte growth factor in patients with gastrointestinal and pancreatic diseases with special reference to inflammatory bowel disease. Res Commun Mol Pathol Pharmacol 1997; 97:25-37). Moreover, in an animal model of IBD, Thatch et al. described that HGF stimulates neovascularization while modulating the intestinal inflammatory response (see, Thatch K A, Mendelson K G, Haber M M, et al. Growth factor manipulation of intestinal angiogenesis: a possible new paradigm in the management of inflammatory bowel disease. *J Surg Res* 2009; 156:245-9). Finally, in a more fundamental study Kanayama et al., investigated the effect of HGF on dextran sulfate sodium-induced colitis and found that HGF gene therapy was effective for the regeneration and repair of injured epithelial cells (see, Kanayama M, Takahara T, Yata Y, et al. Hepatocyte growth factor promotes colonic epithelial regeneration via AKT signaling. Am J Physiol Gastrointest Liver Physiol 2007; 293:G230-9). Whereas these mouse model data are in line with tissue repair effects of higher levels of HGF in acute inflammation, we are looking at patients who are already in a state of mucosal healing by whom higher levels of HGF are no longer needed. Therefore, low HGF levels are highly associated with mucosal healing in this study.

BTC belongs to the EGF family (whose members play an important role in the process of wound healing), though little is known about BTC in IBD. In a study by Chatterton et al. on the anti-inflammatory mechanisms of bioactive milk proteins in the intestine of newborns, BTC was related to inflammation (see, Chatterton D E, Nguyen D N, Bering S B, et al. Anti-inflammatory mechanisms of bioactive milk proteins in the intestine of newborns. Int J Biochem Cell Biol 2013; 45:1730-47). Moreover in a study by Seno et al. it was shown that recombinant BTC had growth promoting activities equivalent to EGF, but was also found to exhibit a growth inhibitory effect on cells overexpressing EGF receptor (see, Seno M, Tada H, Kosaka M, et al. Human beta-cellulin, a member of the EGF family dominantly expressed in pancreas and small intestine, is fully active in a monomeric form. Growth Factors 1996; 13:181-91). Further, BTC has been implicated in the increase of angiogenesis at the site of a wound in the epidermis (see, Schneider M R, Antsiferova M, Feldmeyer L, et al. Betacellulin regulates hair follicle development and hair cycle induction and enhances angiogenesis in wounded skin. J Invest Dermatol 2008; 128:1256-65).

Optimal use of infliximab implies that the lowest level right before the periodic infusion (trough level) must be sufficiently high to exert the full effect of the drug. In the SONIC trial, IFX trough levels have been associated with mucosal healing and in the ACCENT 1 trial IFX trough levels were predictive for a sustained one year response.

In our study, we defined a cut-off of 5.8 µg/ml for assessment of mucosal healing. This cut-off seems clinically relevant since several studies have defined similar cut-offs (see, Marits P, Landucci L, Sundin U, et al. Trough s-infliximab and antibodies towards infliximab in a cohort of 79 IBD patients with maintenance infliximab treatment. J Crohns Colitis 2014; Cornillie F, Hanauer S B, Diamond R H, et al. Postinduction serum infliximab trough level and decrease of C-reactive protein level are associated with durable sustained response to infliximab: a retrospective analysis of the ACCENT I trial. Gut 2014; Imaeda H, Bamba S, Takahashi K, et al. Relationship between serum infliximab trough levels and endoscopic activities in patients with Crohn's disease under scheduled maintenance treatment. J Gastroenterol 2014; 49:674-82.). Moreover, the Trough level Adapted infliximab Treatment (TAXIT) trial describes a trough level between 3 and 7 µg/ml as the optimal interval (see, Vande Casteele N, Compernolle G, Ballet V, et al. Individualized infliximab treatment using therapeutic drug monitoring: A prospective controlled Trough level Adapted infliximab Treatment (TAXIT) trial [abstract ECCO 2012; OP 11])). Since infliximab is a neutralizing antibody directed towards TNF-α, one might expect that TNF-α levels would be decreased in patients who achieved mucosal healing. However, we did not find a significant difference in TNF-α levels in serum samples taken at the time of mucosal healing versus no healing in our cohort. In this study an ELISA based technique was used to measure serum TNF-α levels. However, due to the technical aspects of ELISA, both biologically active as well as potentially physiologically inactive TNF-α (e.g. pro-TNF-α) bound to infliximab can be measured. In a previous study investigating TNF-α levels in chronic venous leg ulcers and its correlation with healing status, it was shown that levels of bioactive TNF-α were not equal to immunoreactive TNF-α levels. Moreover, levels of bioactive TNF-α were higher in patients who achieved healing after infliximab (see, Wallace H J, Stacey M C. Levels of tumor necrosis factor-alpha (TNF-alpha) and soluble TNF receptors in chronic venous leg ulcers—correlations to healing status. J Invest Dermatol 1998; 110:292-6). Another study by Schulz et al. found that the amount of TNF-α remained unchanged in ankylosing spondylitis and rheumatoid arthritis patients after treatment with infliximab (see, Schulz M, Dotzlaw H, Neeck G. Ankylosing spondylitis and rheumatoid arthritis: serum levels of TNF-alpha and Its soluble receptors during the course of therapy with etanercept and infliximab. Biomed Res Int 2014; 2014: 675108.). Based on these studies we can speculate that measuring TNF-α levels after infliximab will not give the desired result of decreased levels in patients achieving mucosal healing. However, the complex biology of TNF-α needs to be taken into account in order to fully understand this phenomenon (see, Tracey D, Klareskog L, Sasso E H, et al. Tumor necrosis factor antagonist mechanisms of action: a comprehensive review. Pharmacol Ther 2008; 117:244-79).

Lastly, VCAM-1 is a cell adhesion molecule that helps regulate leukocyte adherence and infiltration towards inflammatory sites and is elevated in patients with IBD (see, Jones S C, Banks R E, Haidar A, et al. Adhesion molecules in inflammatory bowel disease. Gut 1995; 36:724-30). In a previous microarray study performed by our group, we found that VCAM-1 mRNA expression was significantly increased in inflamed colon of CD patients as compared to controls, and increased levels normalized after treatment with infliximab (see, Arijs I, De Hertogh G, Machiels K, et al. Mucosal gene expression of cell adhesion molecules, chemokines, and chemokine receptors in patients with inflammatory bowel disease before and after infliximab treatment. Am J Gastroenterol 2011; 106:748-61). Moreover, in a study by Soriano et al., it was found that anti-VCAM-1, but not anti-ICAM-1 or anti-MAdCAM-1 antibodies, ameliorated dextran sulfate sodium-induced colitis in mice (see, Soriano A, Salas A, Sans M, et al. VCAM-1, but not ICAM-1 or MAdCAM-1, immunoblockade ameliorates DSS-induced colitis in mice. Lab Invest 2000; 80:1541-51). Furthermore, in a study by Jurisic et al., quantitative lymphatic vessel trait analysis in mice suggested that genetically determined expression differences of VCAM-1 were associated with susceptibility to colon inflammation, which was accompanied by extensive lymphatic vessel changes. VCAM-1 was therefore suggested as a promising therapeutic target for IBD (see, Jurisic G, Sundberg J P, Bleich A, et al. Quantitative lymphatic vessel trait analysis suggests VCAM1 as candidate modifier gene of inflammatory bowel disease. Genes Immun 2010; 11:219-31).

In our study, we chose to combine serum samples that were matched to patients who had complete as well as partial healing at time of sampling. However, after exclusion of the samples matched to partial healing, IFX trough level was no longer an independent predictor of mucosal healing. Nonetheless, HGF, BTC and VCAM-1 remained independently associated with complete mucosal healing. This implies that the markers found to be associated with mucosal healing play a dominant role in the healing process, regardless of the fact whether the healing is partial or complete. From a clinical point of view, having complete healing may not be needed as long as there is (partial) healing (see, Schnitzler F, Fidder H, Ferrante M, et al. Mucosal healing predicts long-term outcome of maintenance therapy with infliximab in Crohn's disease. Inflamm Bowel Dis 2009; 15:1295-301.).

We included serial serum samples for several, but not all patients. Some patients gave 3 serial samples, whereas other gave only one. In multiple regression analysis, we included all serum samples as a separate measurement, matched to mucosal healing status at time of sampling.

In conclusion, we defined a panel of surrogate serum markers that were associated with mucosal healing, whereby the combination of the markers had the strongest association with healing.

Example 3

Serology Panel for Prediction Relapse after Discontinuation of Infliximab in Patients with Crohn's Disease Achieving Clinical Remission INTRODUCTION: Stopping rules for anti-tumor necrosis factor (TNF) therapy are urgently needed. The identification of predictive markers identifying patients at low or high risk for relapse after stopping is therefore warranted. There are limited data concerning the role of non-invasive, serological factors as predictors of relapse after anti-TNF cessation in patients with Crohn's disease (CD).

AIM: We investigated whether a novel serology panel for assessment of wound healing and repair can predict relapse after infliximab (IFX) cessation for clinical remission in patients with CD.

METHODS: This was an observational, retrospective, single-center study. From an electronic database we identified 100 CD patients (57 luminal CD, 40 male, median age at diagnosis 25 years) who discontinued IFX for clinical remission. The majority of patients (n=84) continued on immunomodulators. Relapse was defined as the need to re-introduce medical therapy or surgery. The serology panel included serum TNFα, amphiregulin (AREG), epiregulin (EREG), heparin-binding EGF-like growth factor (HBEGF), hepatocyte growth factor (HGF), heregulin beta EGF domain (HRGB), betacellulin (BTC), epidermal growth factor (EGF), and transforming growth factor alpha (TGFα). These markers were determined in samples taken at the time of IFX discontinuation by Prometheus Laboratories (San Diego, Calif.). A test was considered positive if the titers were higher than the Q3 of the samples measurements: [TNFα, (>12 μg/ml), AREG (>20 U/ml), EREG (>243 U/ml), HBEGF (>12 U/ml), HGF (>74 U/ml), HRGB (>33 U/ml), BTC (>235 U/ml), EGF (>88 U/ml), TGFα (>7 U/ml)].

RESULTS: During a median (IQR) follow up of 9.7 (8.0-11.5) years, 48 out of 100 patients relapsed. A receiver operating characteristic (ROC) analysis did not identify predictive cut-off values for relapse after IFX discontinuation for any of the investigated serological markers. Univariate (Log-Rank) and multiple COX regression analysis revealed borderline significance for positive AREG in predicting relapse (p=0.066 and 0.068 respectively). However, multiple COX regression analysis for a sub-group of patients treated mainly for luminal disease, identified positive AREG as an independent factor predicting relapse after IFX cessation [n=34, p=0.008, HR: 8.1 (95% CI: 1.7-38.1), SN: 80%, SP: 52%, PPV: 22%, NPV: 94%].

CONCLUSION: Positive amphiregulin titers may be associated with relapse in patients who discontinue IFX for clinical remission. AREG is a member of the epidermal growth factor family which is highly expressed only in the active inflamed and not in the normal mucosa of CD patients.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for predicting the likelihood or extent of intestinal mucosal healing in a subject using an endoscopic surrogate measurement score, the method comprising:
   (a) measuring the concentration or level of each of a plurality of biomarkers in a sample obtained from the subject, wherein the plurality of biomarkers consists of a combination of hepatocyte growth factor (HGF), betacellulin (BTC), an anti TNFα drug trough level and vascular cell adhesion molecule 1 (VCAM-1);
   (b) comparing the concentration or level of the plurality of biomarkers to a cut-off value for each biomarker to assign an index value to the concentration or level of each biomarker;
   (c) determining a cumulative biomarker score by applying an algorithm to the index values to determine said endoscopic surrogate measurement score; and
   (d) predicting an increased likelihood or the extent of intestinal mucosal healing in the subject based on the endoscopic surrogate measurement score.

2. The method of claim 1, wherein the subject has inflammatory bowel disease (IBD).

3. The method of claim 2, wherein the inflammatory bowel disease is Crohn's disease or ulcerative colitis.

4. The method of claim 1, wherein measuring in step (a) comprises performing a proximity dual detection assay, an immunoassay or a homogeneous mobility shift assay (HMSA).

5. The method of claim 4, wherein the proximity dual detection assay is Collaborative Enzyme Enhanced Reactive Immunoassay.

6. The method of claim 1, wherein the index value is from 0 to 4 and based on whether the concentration or level of the biomarker is above or below the cut-off value such that the value of 4 is positively associated with intestinal mucosal healing.

7. The method of claim 1, wherein the cut-off value for HGF is less than about 11.42 CU/ml.

8. The method of claim 7, wherein the cut-off value for HGF is from about 1 CU/ml to about 11.42 CU/ml.

9. The method of claim 1, wherein the cut-off value for BTC is greater than about 11.44 CU/ml.

10. The method of claim 9, wherein the cut-off value for BTC is from about 11.44 CU/ml to about 100 CU/ml or more.

11. The method of claim 1, wherein the cut-off value for VCAM-1 is less than about 420 μg/ml.

12. The method of claim 11, wherein the cut-off value for VCAM-1 is from 1 μg/ml to about 420 μg/ml.

13. The method of claim 1, wherein comparing in step (b) comprises applying an algorithm incorporating the concentration or level of each of the plurality of biomarkers.

14. The method of claim 1, wherein the index value is from 1 to 4 based on a quartile score, such that quartile 1 is given the index value of 4, quartile 2 is given the index value of 3, quartile 3 is given the index value of 2 and quartile 4 is given the index value of 1.

15. The method of claim 1, wherein the algorithm of step (c) comprises summing the index values to determine the cumulative biomarker score.

16. The method of claim 1, wherein the cumulative biomarker score of 4 predicts an increased likelihood of intestinal mucosal healing in the subject.

17. The method of claim 1, wherein the subject is receiving a TNFα inhibitor.

18. A method for predicting the likelihood of intestinal mucosal healing in a subject, the method comprising:
   (a) measuring the concentration or level of each of a plurality of biomarkers in a sample obtained from the subject, wherein the plurality of biomarkers consists of a combination of hepatocyte growth factor (HGF), betacellulin (BTC), the anti-TNFα trough level, and vascular cell adhesion molecule 1 (VCAM-1);
   (b) comparing the concentration or level of the plurality of biomarkers to a cut-off value for each biomarker to assign an index value to the concentration or level of each biomarker;

(c) determining a cumulative biomarker score by applying an algorithm to the index values to determine said endoscopic surrogate measurement score; and
(d) predicting an increased likelihood or the extent of intestinal mucosal healing in the subject based on the endoscopic surrogate measurement score.

19. A method for determining an endoscopic endoscopic surrogate measurement score in a subject, the method comprising:
(a) measuring the concentration or level of each of a plurality of biomarkers in a sample obtained from the subject, wherein the plurality of biomarkers consists of a combination of the following biomarkers, which include hepatocyte growth factor (HGF), betacellulin (BTC), an anti TNFα drug trough level and vascular cell adhesion molecule 1 (VCAM-1);
(b) comparing the concentration or level of the plurality of biomarkers to a cut-off value for each biomarker to assign an index value to the concentration or level of each biomarker;
(c) determining a cumulative biomarker score by applying an algorithm to the index values; and
(d) determining the endoscopic surrogate measurement score in the subject based on if the cumulative biomarker score.

20. A method for determining an endoscopic surrogate measurement score in a subject, the method comprising:
(a) measuring the concentration or level of each of a plurality of biomarkers in a sample obtained from the subject, wherein the plurality of biomarkers consists of a combination of hepatocyte growth factor (HGF), betacellulin (BTC), tumor-necrosis factor-related weak inducer of apoptosis (TWEAK) and vascular cell adhesion molecule 1 (VCAM-1);
(b) comparing the concentration or level of the plurality of biomarkers to a cut-off value for each biomarker to assign an index value to the concentration or level of each biomarker;
(c) determining a cumulative biomarker score by applying an algorithm to the index values; and
(d) determining the endoscopic surrogate measurement score in the subject based on the cumulative biomarker score.

21. The method of claim 20, wherein the cut-off value for TWEAK is greater than about 20.62 CU/ml.

22. The method of claim 20, wherein the cut-off value for TWEAK is from about 20.62 CU/ml to about 100 CU/ml or more.

23. The method of claim 20, wherein the quartile scores for BTC and TWEAK are inverted in the algorithm.

\* \* \* \* \*